(12) United States Patent
Ramig et al.

(10) Patent No.: US 7,762,264 B1
(45) Date of Patent: Jul. 27, 2010

(54) TOTAL COMMUNICATIONS AND BODY THERAPY

(75) Inventors: Lorraine Ramig, Boulder, CO (US);
Cynthia M. Fox, Tucson, AZ (US);
David McFarland, Montreal (CA);
Becky G. Farley, Tucson, AZ (US)

(73) Assignee: LSVT Global, Inc., Tucson, AZ (US)

( * ) Notice: Subject to any disclaimer, the term of this patent is extended or adjusted under 35 U.S.C. 154(b) by 880 days.

(21) Appl. No.: 11/300,604

(22) Filed: Dec. 14, 2005

Related U.S. Application Data

(60) Provisional application No. 60/635,773, filed on Dec. 14, 2004.

(51) Int. Cl.
*A61B 19/00* (2006.01)
(52) U.S. Cl. ..................................... 128/898
(58) Field of Classification Search ................. 128/898; 601/1
See application file for complete search history.

(56) References Cited

OTHER PUBLICATIONS

Farley, Becky G. "Think Big, from Voice to limb Movement Therapy." Seventh International Conference on Spoken Language Processing (2002).*
Hamilton, Lynn M. "There Is Hope." Autism Research Institute (2003).*
Solomon, Nancy Pearl et al. "Intensive Voice Treatment and Respiration Treatment for Hypokinetic-Spastic Dysarthria After Traumatic Brain Injury." American Journal of Speech—Language Pathology 10 (2001): 51-64.*
Schreibman, Laura et al. "Focus on Integration: The Future of the Behavioral Treatment of Autism." Behavior Therapy 32 (2001): 619-632.*
LSVT Global. "Speech Exercise Video Product FAQ's." LSVT Global 2004 <http://gleecoinc.com/sp-bin/spirit?PAGE=25>.*
Ramig, Lorraine Olson. "Treatment of Speech and Voice Problems Associated with Parkinson's Disease." Topics in Geriatric Rehabilitation 14 (1998): 28-43.*
Ramig et al. "Intensive speech treatment for patients with Parkinson's disease: Short- and long-term comparison of two techniques." Neurology 47 (1996): 1496-1504.*

* cited by examiner

*Primary Examiner*—David Isabella
*Assistant Examiner*—Andrew Iwamaye
(74) *Attorney, Agent, or Firm*—The Ollila Law Group LLC

(57) ABSTRACT

A therapy program for speech and movement disorders in which the patient is directed to concentrate on the amplitude of their speech and movement. The program may be directed solely to speech, solely to movement, or simultaneously to speech and movement. The program is applied in 16 sessions over a 4-week period, with each session including a half-hour on fundamental tasks and a half-hour on more complex or hierarchical tasks. Further, the patient is helped to calibrate the amplitude of their speech and movement.

20 Claims, 17 Drawing Sheets

| | WEEK 1 | WEEK 2 | WEEK 3 | WEEK 4 |
|---|---|---|---|---|
| | | DAILY TASKS | | |
| | SPEAKING WORDS AND PHRASES | SPEAKING SENTENCES | SPEAKING PARAGRAPHS | CONVERSATION |

FIG.10

| | WEEK 1 | WEEK 2 | WEEK 3 | WEEK 4 |
|---|---|---|---|---|
| | | DAILY TASKS | | |
| | HIERARCHICAL TASKS I | HIERARCHICAL TASKS II | HIERARCHICAL TASKS III | HIERARCHICAL TASKS IV |

FIG.11

TOTAL COMMUNICATIONS AND BODY THERAPY

CROSS-REFERENCE TO RELATED APPLICATION

This application claims priority from U.S. Provisional Patent Application No. 60/635,773, filed Dec. 14, 2004, entitled "Integrated total-body movement therapy program to enhance speech, voice, movement and learning in individuals with motor and other cognitive linguistic disorders", the contents of which are incorporated herein by reference.

BACKGROUND

Therapy such as speech therapy and physical therapy can often be a powerful tool in the treatment of many diseases and injuries. Therapy can be provided either alone or in conjunction with other medical treatments or interventions. However, pharmaceutical and/or surgical interventions are often not sufficient for improving physical limitations (e.g., speech and motor limitations) associated with many medical conditions. Behavioral therapeutic programs can therefore be a key tool in a patient's rehabilitation and recovery. For example, speech therapy is often used to improve speech/language impairments in patients with Parkinson's disease whose speech production deteriorates during the disease process. Similarly, physical therapy is often used to reduce symptoms of movement disorders in patients with Parkinson's disease.

However, speech and physical therapy may have several limitations when treating various neurological disorders, such as Parkinson' disease. First, speech and physical therapy are always given as separate treatment by separate professionals. Second, the overall treatment program and components thereof are typically targeted only to the symptoms of the patient. Third, treatments are typically of low intensity in that various tasks may only be performed once in each session and treatment sessions may only be delivered once or twice per week. Fourth, treatments typically have multiple foci, such as volume, rate, breath support, and enunciation for speech therapy and balance, gait, and reaching for physical therapy. Fifth, each subcomponent of a breakdown (e.g., in communication, speech, language, and swallowing and in physical therapy, balance, gait, mobility) are trained individually by specific exercises targeting each subcomponent. These drawbacks are explored further below.

It is a common practice worldwide for patients to receive separate therapy from therapists of different disciplines to treat limb and speech motor disorders. For example, a patient with Parkinson's disease may see a speech therapist for communication disorders, a physical therapist for limb and gait disorders, and an occupational therapist for improving activities of daily living, such as eating and dressing. These therapeutic interventions often target a specific motor system, for example the speech motor system, the language system, or the limb motor systems (e.g., reaching, walking) of a patient in isolation and usually by distinct therapists or teachers. Often, these separate therapies are delivered at different times (e.g., receive physical therapy several months after receiving speech therapy).

Most often, the specific exercises used in treatment are chosen based upon a patient's response to a detailed assessment, evaluating each subcomponent of the production system. For example, the speech clinician evaluates the speech production system (respiratory, phonatory, articulatory and velopharyngeal systems), the language system (sematics, syntax, phonology, pragmatics) and swallowing and any breakdowns observed are targeted in treatment with specific exercises directed to the specific breakdown. For example, tongue weakness may be addressed with tongue strengthening exercises, soft volume may be addressed by breathing exercises and syntax may be addressed by exercises focusing on the specific linguistic deficit. Similarly in movement, the physical therapist evaluates posture, upper and lower extremities and balance and any breakdowns observed are targeted in treatment with exercises directed to the specific breakdown. For example, lower extremity weakness would be targeted by specific leg strengthening exercises and upper extremity weakness would be targeted by specific arm strengthening exercises When therapists try to teach patients to improve their disorder they often use multiple instructions to achieve the speech or limb motor goal. For example, during speech treatment, patients may be cued to "slow down, take a deep breath, over articulate, and talk louder." In separate treatment sessions, the same patient may have multiple instructions to improve physical functioning, such as "scoot forward to edge of chair, lean forward, and push up." Both traditional speech and physical therapy programs have limited long-term efficacy. Patient compliance with programs is variable, due to often limited positive impact on function, perhaps related to difficulty in carrying out multi-step tasks and practicing multiple treatment regimes in individuals who may have cognitive challenges to learning.

An example of a neurological disorder is Parkinson's disease (paralysis agitans). Parkinson's disease is a neurodegenerative disease of brain, specifically an area called the substantia nigra pars compacta (an area in the basal ganglia of the brain that produces a neurotransmitter called dopamine). The disease involves a progressive loss of dopamine, resulting in a movement disorder of the extrapyramidal system, which controls and adjusts communication between neurons in the brain and muscles in the human body. It also commonly involves disturbances of sensory systems related to the awareness of movement. Disordered voice and speech characteristics of individuals with Idiopathic Parkinson's Disease (IPD) are frequently related to the motor signs of the disease (rigidity, bradykinesia, hypokinesia, tremor). Reduced amplitude of movement (hypokinesia) and slowed movement (bradykinesia), which are observed across motor systems in individuals with IPD, have been associated with "the cortical motor centers being inadequately activated by excitatory circuits passing through the basal ganglia" (Penny & Young, 1983) and subsequent reduced drive to motoneuron pools. This may be manifest in reduced movement during walking (reduced arm swing, shuffling gait), writing (micrographia) and talking (soft voice) (Beneke et al., 1987; Hallet and Khoshbin, 1980; Tatton, Eastman, Bedingham, Verrier, & Bruce, 1984; Wisendanger and Rüegg, 1978).

While the causes of neurological disorders such as Parkinson's disease are not entirely understood, one theory about what causes movement problems in a patient suffering from Parkinson's disease relates to their inadequate cortical drive (activation) to the muscle resulting in inadequate and variable force production. The movements that are most impaired are the ones most automated or repetitive (e.g. walking, sit-to-stand, speaking, etc.). Due to the slow onset, patients adapt to slower and smaller movements and fail to self-correct their movement patterns, despite having the potential to move and speak at normal bigness/loudness. When asked to perform movements of normal bigness/loudness they do so; but report it is effortful and that the movement feels too big/loud or abnormal.

A patient with Parkinson's disease may have symptoms in several areas, such as speech, movement and/or motor control. Therefore, a patient with Parkinson's disease is often treated with a plurality of therapies designed to target the patient's symptoms and help him regain at least minimal functionality in the affected area or areas. Some common therapy practices include speech/language therapy, physical therapy, occupational therapy and co-therapy. Co-therapy can involve two or more therapists working with a patient on separate tasks in a particular therapy session.

Some techniques used in these therapy sessions include, using exercises that practice one skill at a time, breaking down skills into particular component skills to make them easier to perform, and focusing on performing the skill correctly. Practicing one skill at a time and breaking down skills into particular component skills are techniques that allow a therapist to adjust the therapy session to match a particular patient's level of functioning in a particular area (e.g., dexterity, motor control, or enunciation). For example, a speech therapist may use a book of standard phrases (e.g., dysarthria word lists) that uses random speech material for speech practice but does not target a particular problem area (e.g., enunciating each syllable). The books of phrases may vary based on the difficulty level and the therapist will often choose a book that is appropriate to a particular patient's level of speech quality/functioning. Therapists also often ask the patient to practice the skills until the patient is able to perform the skills or random material at a certain level correctly. After the therapist is satisfied that the patient can perform the skill or level correctly, the therapist advances the patient to a new skill or skill level. In speech therapy, this new skill or set of skills may be contained in a different book of standard phrases. A disadvantage of teaching only skill-level specific skills to patients is that new skills must be learned when the patient advances past the appropriate level of a skill. Learning a new skill is inefficient because of the time and effort it takes simply to learn the new skill before practice is able to begin on the therapeutic techniques embodied in the new skill.

In addition, speech treatment typically focuses on one global skill area at a time. For example, in speech therapy, motor speech practice is separately trained from language and cognitive practice as well as swallowing problems. A speech clinician uses different techniques and materials as well as targets for the patient to train the speech motor system, the language system, and the swallowing function. A disadvantage of this is that the integration of these subcomponents into functional speech production is uncommon.

Another broad category of therapy techniques uses external cues (visual, auditory, attentional/cognitive) to help a patient understand how loud/quickly to speak or where to place her hands/feet. These techniques may also be called compensatory strategies with external cues. In order to counteract a patient's difficulty in producing the adequate muscle activation (force) to perform a task correctly, a therapist may teach the patient compensatory strategies using external cues. An example of these external cues may include strips of masking tape set on floors at regular intervals to provide visual feedback to guide the patient to compensate his/her movement with larger steps until it outwardly conforms to the placement of the tape. Other example may include a metronome used to provide a rhythm cue to guide the patient to compensate his/her speech to a faster/slower rate to conform to the metronome or a voice light to provide a sound level cue, allowing the patient to compensate his/her speech to conform to the loudness level required by the voice light. A disadvantage of using an external cue is that it requires a logical process to be performed by the patient. First, the patient must recognize the cue as an external reminder (e.g., for guiding movement or speech). Second, the patient must determine whether the outward expression of the skill or function he is performing (e.g., movement or speech) matches the guidance provided by the cue (e.g., length of the movement as marked out by strips of masking tape, loudness of the sound as provided by the sound level light, or rhythm of the sound as provided by the metronome). Third, the patient must adjust the effort given to the skill or function, if needed. Another disadvantage is that the patient who uses external cues as a guide for coping with reduced functionality becomes dependent on these external cues and must think to reference the external cues in order to use their guidance. Another disadvantage of using external cues is that they're often difficult to replicate outside of a controlled setting. For example, masking tape must be applied to services in order to be used as an external cue and metronomes/voice lights need to be carried, set up, and calibrated.

Therapy programs are often designed to target specific parts of a skill that is lacking in a patient, or even random words out of a list (in the case of speech therapy). Thus, therapy techniques may be of a type that the patient is unable to perform the techniques outside of the therapy session. The techniques may also be specially designed for use within the therapy session and/or may not be suitable for use or practice in a real-world session. For example, a phrase practiced in a therapy session and/or at home may be inappropriate for the patient to use in a conversation at a grocery store or in a phone call to a friend.

Therapy techniques may be applied to patients with a range of abilities. It is common for a therapist to guide a patient to perform a technique that is appropriate for what the patient can comfortably perform. Common therapy techniques include a focus on training the patient to perform a skill that allows the patient to better cope with his reduced functionality. Training a patient to cope with reduced functionality may avoid addressing or reversing the cause of the reduced functionality, and may, therefore, allow the functionality to become further reduced. Also, training a patient to cope with reduced functionality, even if successful, may result in the patient becoming dependent on the methods required to cope with the reduced functionality and/or may limit the patient to that level of functionality. If the patient is dependent on these methods, the patient may have limited flexibility in planning when and how to perform the skills that allow him to cope with his reduced functionality. Furthermore, if the patient's functionality is further reduced, he may have to re-learn the coping skills or may have to learn entirely new skills in order to cope with his further reduced functionality. Several other factors may reduce the amount of therapeutic progress attainable in a given period of time. For example, to adjust to a patient's decreased level of functioning, therapy techniques for neurological disorders are often practiced at a low intensity, for example one therapy session per week, and may continue for an extended period of time such as a year or more.

SUMMARY

One aspect of the invention is related to a method of providing physical therapy to a patient suffering from a neurological disorder, neurological condition, or effects of natural aging process. The method includes instructing the patient to perform movement tasks while focusing solely on the amplitude of their response.

The amplitude may be the size of the limb and body movements the patient generates. The tasks performed may be simultaneous speech and movement tasks and the amplitude of the speech portion may be the sound pressure level the patient generates and the amplitude of the movement portion may be the size of the limb and body movements the patient generates.

Another aspect relates to a method of treating symptoms of a neurological disorder, neurological condition, or effects of natural aging process. The method includes instructing for a patient to perform a first task focusing on an amplitude of the first task; and performing sensory calibration. The sensory calibration includes observing an amplitude of the first task as performed by the patient; asking the patient to describe a perceived effort related to amplitude of the first task as performed; determining a fit between the perceived effort of amplitude of the first task and the amplitude of the first task as observed; and communicating with the patient a sensory calibrating instruction based on the fit.

The asking operation may include a request to perform a second task. The method may further include providing an instruction wherein the patient is reminded to focus on amplitude and the perceived effort of amplitude if the patient does not perform the second task at a sufficient amplitude. The method may further include giving a pre-task sensory calibrating instruction before the directing. The sensory calibrating instruction may include directing the patient to perform the task again while attempting to attain a different perceived amplitude. The first task may be a compound task. The first task may be a task suggested by the patient.

Another aspect relates to a method of providing therapeutic instruction in speech therapy. The method includes stimulating a first vocal response in a patient through instructing the patient to vocalize a first sound at an amplitude greater than 75 dB SPL at 30 cm; shaping a second vocal response in the patient through instructing the patient to vocalize the first sound at an amplitude greater than 75 dB SPL at 30 cm and to focus on a particular aspect of quality while vocalizing the first sound; stabilizing a third vocal response in the patient through instructing the patient to vocalize the first sound at an amplitude greater than 75 dB SPL at 30 cm and to focus on continuing to vocalize the first sound for a particular duration; instructing the patient to vocalize a second sound at a pitch near an upper limit of the patient's range; instructing the patient to vocalize the second sound at a pitch near a lower limit of the patient's range; soliciting from the patient a first phrase of interest to the patient; modifying the first phrase in accordance with a therapeutic objective for the patient if appropriate; directing the patient to recite the first phrase at an amplitude greater than 75 dB SPL at 30 cm; directing the patient to recite the first phrase at an amplitude greater than 75 dB SPL at 30 cm and to focus on a particular aspect of quality while reciting the first phrase; and providing sensory calibration feedback. The feedback includes: listening to the patient vocalize a third sound or recite a second phrase; receiving an indication of a perceived amplitude of the third sound or the second phrase; determining a relative amplitude of the third sound or the second phrase compared to the perceived amplitude; and instructing the patient to attempt to achieve a desired perceived amplitude while vocalizing a subsequent sound or reciting a subsequent phrase.

The subsequent sound may be substantially similar to the third sound. The subsequent phrase may be substantially similar to the second phrase.

Another aspect relates to a method of treating symptoms of a neurological disorder, neurological condition, or effects of natural aging process. The method includes directing the patient to perform a vocalization task and a movement task simultaneously, while focusing on an increased amplitude of both the tasks; observing the patient in the performance of both the tasks; receiving a perceived effort evaluation from the patient regarding the tasks; providing feedback to the patient regarding an amplitude of both the tasks as observed; and after providing feedback, directing the patient to perform both the tasks again.

All of the therapy may be performed by a single therapist.

Another aspect relates to a method of treating symptoms of a neurological disorder, neurological condition, or effects of natural aging process. The method includes training a skill; inducing motor overflow; and training minimum functioning of skill while allowing motor overflow to continue.

Another aspect relates to a method of treating symptoms of a neurological disorder, neurological condition, or effects of natural aging process. The method includes having the patient perform the same core tasks at each of multiple therapy sessions in at least a first period, a second period, and a third period of a treatment plan for the patient; further having the patient perform different hierarchical tasks at the multiple therapy sessions in at least the first period, the second period, and the third period of the treatment plan for the patient.

Another aspect relates to a method of treating symptoms of a neurological disorder, neurological condition, or effects of natural aging process. The method includes instructing the patient to perform speech language deficit tasks while focusing solely on the amplitude of their response; wherein the speech language deficit tasks include at least one of semantic, syntactic, and phonological exercises.

The amplitude may be the sound pressure level the patient generates.

Areas of focus in communication therapy—these would be treated separately (e.g., work on language skills only; work on voice skills only) even if a patient has problem with speech, voice, swallowing, and cognition. A therapist may decide which is most disordered area and target that first—then move to the next area of need in a sequential progression.

Speech (articulation)
Voice (phonation)
Language (semantics, syntax)
Cognitive (memory)
Pragmatics (social interaction)
Swallowing
Movement Areas of focus in movement therapy would be treated separately as described for speech:

Gait (walking)
Mobility (getting in/out of car)
Balance
Strength
Range

Within each of these areas of focus, therapists often further break down the skill to determine what is the most disordered subcomponent of speech or language and then target that aspect first and move sequentially to the next area of need.

Speech: oral motor strength/coordination, voice onset timing, respiratory support Voice: posture, breath support, vocal fold adduction, mouth opening, resonance The breakdown above is similar for physical therapy
This is a RADICAL change on many levels
We propose training
Communication and Movement Simultaneously
Training areas of focus for Communication and Movement simultaneously Training subcomponents of areas of focus simultaneously 1. Single focus of therapy (for the patient) on amplitude (Loud, big, big and loud) REGARDLESS of most disordered area of communication or movement breakdown 2. Address multiple areas of communication therapy simultaneously with focus only on LOUD (e.g., in PD address speech, voice swallowing simultaneously; in Down syndrome address speech, voice, language and pragmatics simultaneously) Thus we do not first fix the articulation, then improve the voice quality and then transfer those skills to pragmatics. WE treat all simultaneously through LOUD—implicitly embedding language or pragmatic targets into the hierarchy practice (no explicit attention drawn to these goals)

3. Address all subcomponents of an area of communication simultaneously. For improving Voice we train one target LOUD! The only focus for the patient is LOUD. Through shaping the clinician models good posture, breath support, an open mouth, etc.—but never explicitly draws a patients attention to these features—only LOUD. In contrast, traditional therapy would for Voice, a clinician would break it apart into posture, breath support, vocal fold adduction, mouth opening, resonance, and may address each of these individually and sequentially.

4. Training different areas of rehabilitation simultaneously, Communication and Movement, as we are proposing with Big and LOUD.

BRIEF DESCRIPTION OF THE DRAWINGS

FIG. 10 is a depiction of the different components of the therapy technique that are utilized over the course of a 4-week speech treatment program.

FIG. 11 is a depiction of the different components of the therapy technique that are utilized over the course of a 4-week movement treatment program.

DETAILED DESCRIPTION

Figure 1:
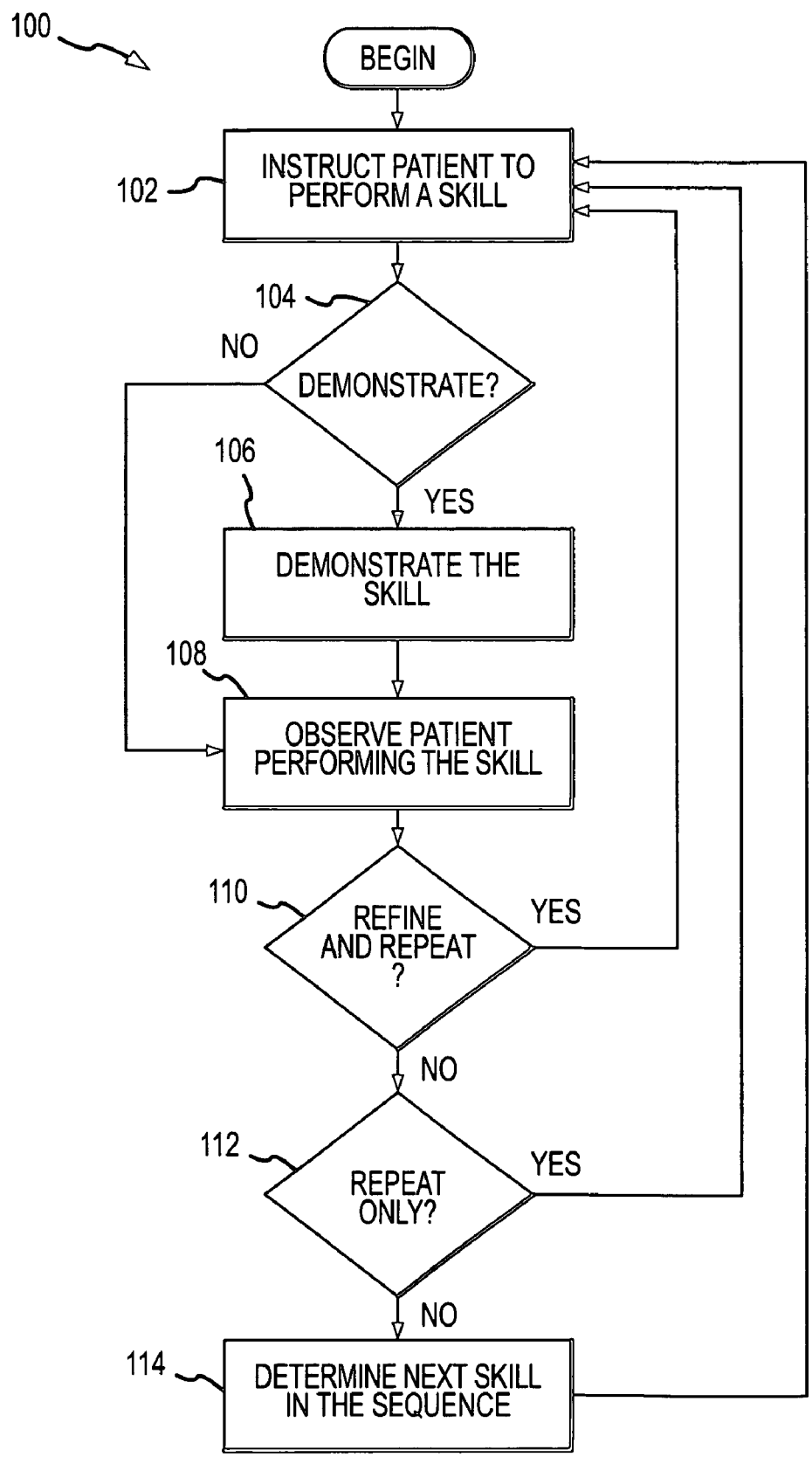
FIG. 1 is a flow chart of a therapy session.
Figure 2:
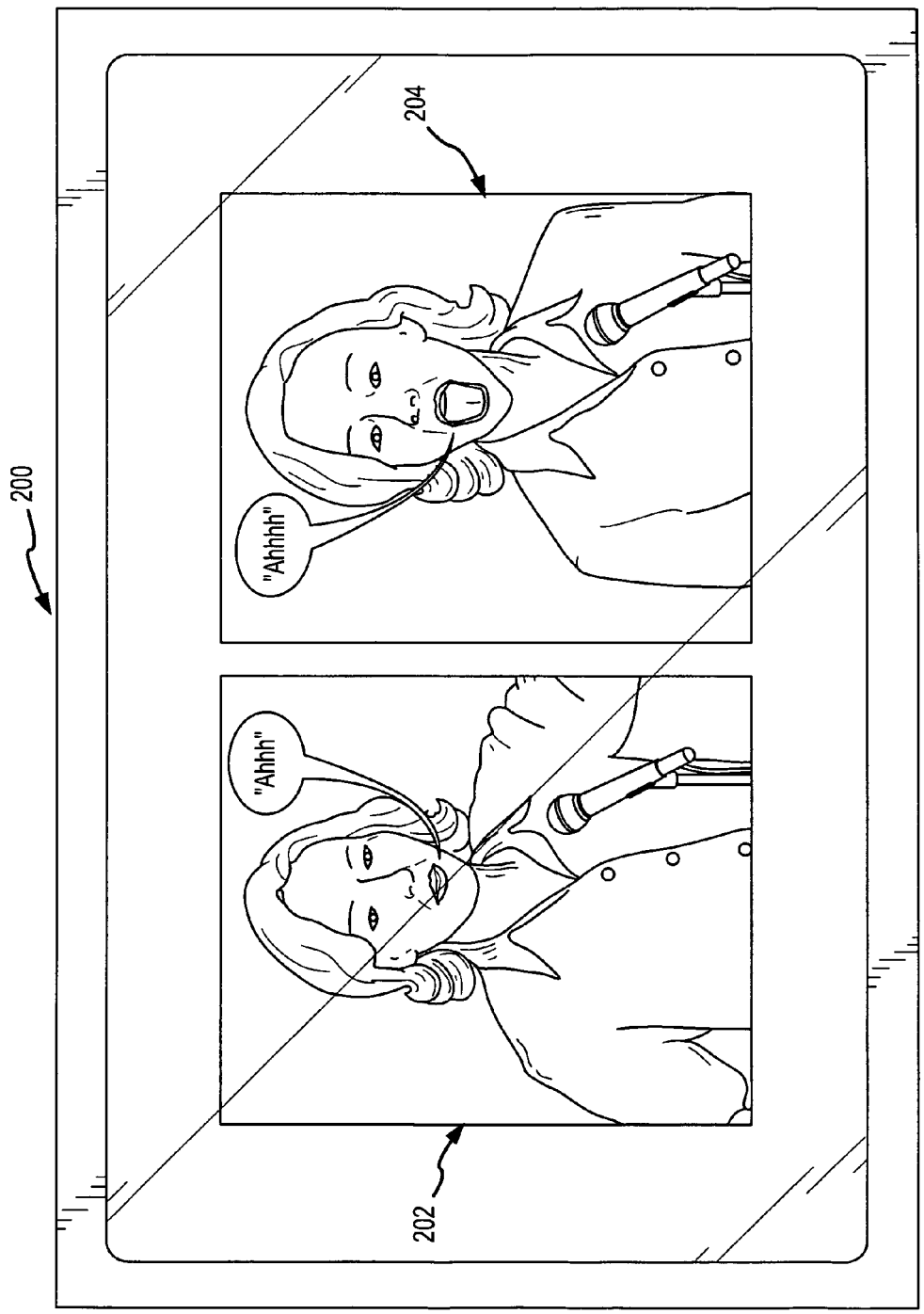
FIG. 2 is a split screen display comparing two different performances of a fundamental vocal skill, at different amplitude levels.

Reference will now be made to the accompanying drawings, which assist in illustrating the various pertinent features of the present invention. Although the present invention will now be described primarily in conjunction with a behavior treatment method and apparatus, it should be expressly understood that the present invention may be applicable to other applications where therapeutic treatment is required/desired. In this regard, the following description of a therapy technique is presented for purposes of illustration and description. Furthermore, the description is not intended to limit the invention to the form disclosed herein. Consequently, variations and modifications commensurate with the following teachings, and skill and knowledge of the relevant art, are within the scope of the present invention. The embodiments described herein are further intended to explain best modes known of practicing the invention and to enable others skilled in the art to utilize the invention in such, or other embodiments and with various modifications required by the particular application(s) or use(s) of the present invention.

The therapy techniques described herein include a therapist guiding a patient in speaking louder and performing tasks bigger, and stretching the patient's limits of comfort in doing so. Therapy of this type may be referred to as behavioral treatment and the behavioral treatment method and apparatus described herein relate generally to the treatment of neurological disorders, neurological conditions, natural aging process, and their symptoms across their life span. Furthermore, this type of therapy may be related to other disorders of communication or movement due to foreign language acquisition (including linguistic components and dialect, accent), orthopedic impairments, psychological impairments, or to enhance overall normal function across the life span. The treatment includes a therapy program that includes guided therapy sessions comprised of tasks performed by a patient at a desired amplitude (e.g., bigger movements and louder speech with increased level of perceived exertion) and feedback given to the patient regarding the actual amplitude of the patient's performance (e.g, how big her movements were or how loud her voice was). The tasks performed by patient may include, by way of example, speaking, moving, grasping, and looking in a particular direction. The tasks may also be combined to form other tasks, for example, speaking while walking and carrying an object (e.g., a clipboard holding something to read). There is one explicit GLOBAL target in therapy sessions: increased amplitude of movement or speech. The global target addresses multiple levels of communication and movement therapies, and addresses multiple subcomponents of movement (posture, swallowing, respiration, speed, amplitude, etc.) and speech.

The treatment program may address: primarily communication disorders; primarily movement disorders; or both communication and movement disorders simultaneously. The therapy techniques in each program are designed to increase the amplitude of the patient's speech and movement to within normal ranges. Each of the programs includes four weeks of four one-hour sessions each week, likely on different days of the week (e.g., Monday through Thursday). Each of the one-hour sessions includes a first half in which the same daily tasks are practiced everyday and a second half in which a hierarchy of progressively-difficult, different tasks are practiced, depending upon the week of the therapy session.

There are many possible treatment programs that may be developed using the therapy techniques described, and those treatment programs can be adjusted to fit patients with different diseases, injuries, levels of functioning, age, etc. The treatment programs can even use technology to accommodate patients who cannot easily travel to see a therapist. The therapy programs are built from components that may be combined in several ways to create a therapy program that is both cohesive and effective. These components include guided practice sessions, virtual therapy using automated screening protocols, and therapy sessions via computer. For example, the use of a split screen and/or simultaneous playback to allow a patient to recognize the difference between a desired amplitude and an actual amplitude he is performing presently. A therapist and a patient may use such an apparatus to better understand the desired amplitude the patient is trying to achieve.

Other important components of the therapy programs are skills that do not require a patient to think about the verbal instructions given by the therapist. This may be referred to as minimization of cognitive loading on a patient, and may be achieved through a therapist demonstrating a particular skill for the patient. For example, instead of providing verbal instructions to the patient (e.g., sit up straight, take a deep breath, slow down, over-articulate, and be loud), the therapist may demonstrate the skill and ask the patient to "do what I do." The therapist guides the patient through modeling the desired skill rather than having to translate the desired skill into instructions. Furthermore, the patient does not need to interpret verbal instructions and/or translate them into an understanding of the specific performance that is requested. Instead, the patient only has to pay attention to the obtaining their goal—increased amplitude of speech or movement—it should feel like they are moving too big or speaking too loud. Their target is "how does it feel?" The therapist may use a split screen apparatus to demonstrate a skill, for example, through filming herself while she demonstrates the skill and displaying it side by side with a recording of the patient performing the skill. Either or both of the therapist's and the patient's performance may be displayed from a recorded version or from a live feed from a camera for movement or speech, or in the case of speech, from an audio recording.

Another component of the therapy program is that, while guiding the patient through a skill, the therapist will correct behavior that is harmful to a patient or his therapeutic goals. The therapist will distinguish from behavior (e.g., speech or movement) that is detrimental to the therapy (e.g., slows the patient's progress) and behavior that may seem incorrect, but is actually expected by trained therapists when a patient performs a task with a high level of exertion. This type of behavior is sometimes called "motor overflow" by therapists. The therapist uses her ability to discern between improper movement and movement that is result of motor overflow to create this unique feature of the therapy. Motor overflow can occur in a patient as a result of the patient's attempt to exert increased effort in performing a task (e.g., vocalization, movement of limbs, a combination thereof). A therapist who distinguishes between improper movement (i.e., unsafe mechanical alignment) and motor overflow (i.e., incoordination) may choose to discourage the improper movement and allow the motor overflow to continue, trusting that the motor overflow will subside as the patient learns the most efficient way to perform the task.

Figure 4:
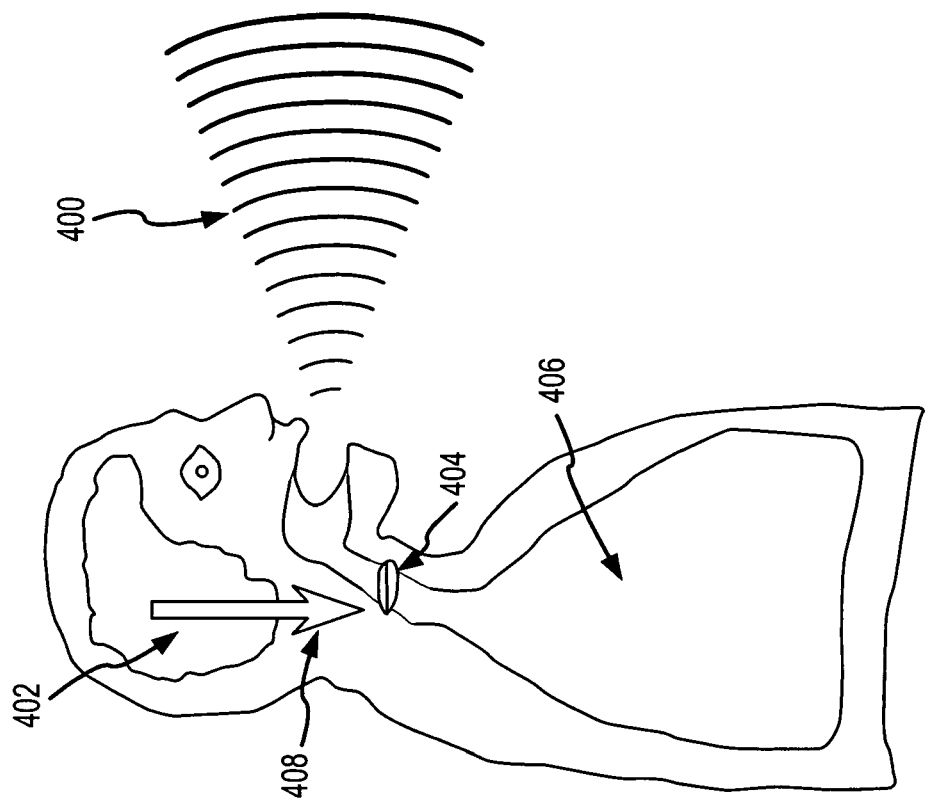
FIG. 4 is a depiction of some of the processes present in a patient performing a loud vocal skill.
Figure 3:
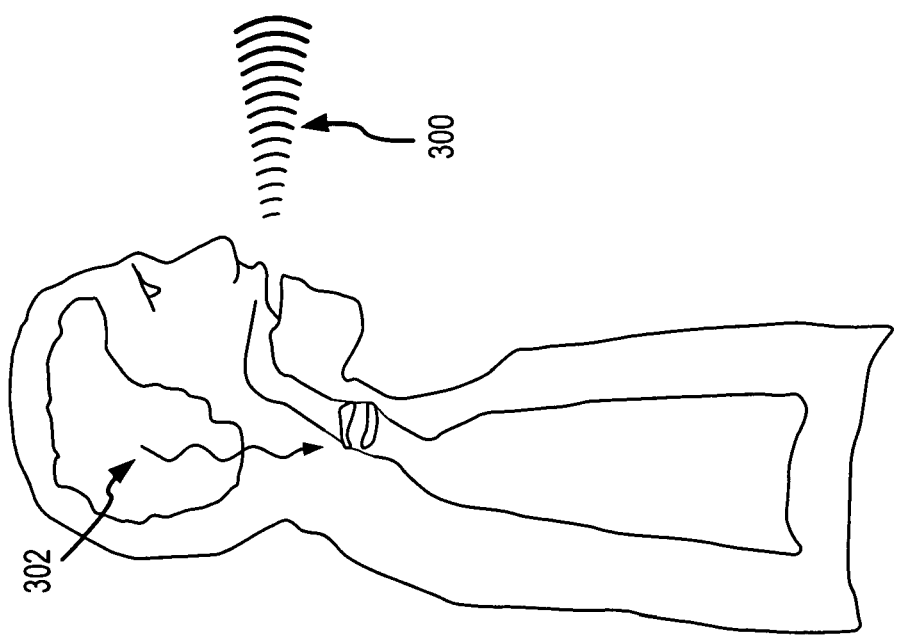
FIG. 3 is a depiction of some of the processes present in a patient performing a quiet vocal skill.

The skills practiced by patients in the therapy programs include fundamental skills such as the patient making an "Ahhhhh" sound with increased loudness level and for as long as he can, thus stressing the amplitude of the performance in several ways (see generally, FIGS. 3 and 4). The behavioral treatment method and apparatus define this type of skill as a group of exercises with an emphasis on amplitude of performance, such as the extent of limb movement or the loudness of vocalization. Amplitude may be stressed in the beginning of a therapy session followed by repetitions to stabilize the ability to achieve that amplitude in the exercises. For example, the exercises may develop muscles (e.g., 404), organs (e.g., 406), and the cortices of the brain (e.g., 402) responsible for the control of many functions in the human body and for the perception of effort (e.g., 408) by the patient.

Complex exercises are also used in the therapy programs. The behavioral treatment method and apparatus defines a group of complex exercises including skills that are useful outside of the therapy session. This group includes tasks that the patient has suggested, tasks that are of particular importance to the patient, and/or functional tasks that may be useful in the real-world. FIGS. 8a-8d provide some examples of complex tasks. Performing the complex exercises may require the patient to use multiple skill sets including, for example, speech and motor control skills. For example, a complex exercise includes opening a wallet, taking money out of the wallet, handing money to someone, saying "here you go," receiving money in return, saying "thank you," putting money back into the wallet, and putting the wallet into a pocket. There are therapeutic advantages and benefits gained from the use of complex exercises which will be described further below, as will the distinctions and advantages over the prior art practice of avoiding "dual task" exercises in therapy.

The therapy programs that use some of the techniques described herein may follow an intensive schedule due, in part, to the nature of the techniques that the program incorporates. The behavioral treatment method and apparatus described herein may use an intensive schedule (e.g., 16 sessions, four times a week for four weeks), focusing roughly the first half of each session on exercises relating to performance of relatively simple tasks (the first group of exercises) performed at an increased or potentially maximum amplitude. These tasks provide the daily calibration of motor output and sensory recognition that is necessary to maintain improvements and prevent the continual deterioration associated with a degenerative disease. Roughly the first half of each session, therefore, is devoted to this over-learning and calibration and this first half of each session is repeated throughout the entire treatment process, even as the patient improves in his functioning. Roughly the second half of each session is devoted to the performance of exercises that are more complex than those practiced in the first half (e.g., skills training) and, therefore, the second half of each session aids in applying some of the learning from the first half to real-world situations. The exercises in the second half are often used by the therapist as "homework assignments" or "carryover tasks" for the patients. These assignments are used in the therapeutic process as situations for the patient to practice some of the skills developed in the second half of the sessions in situations that are meaningful to the patient and outside the controlled environment of the therapy session. Furthermore, the assignments are an integral part of the therapeutic process as practicing the skills and exercises he has learned in the real world provides immediate positive benefits in the patient's life. This helps to enforce calibration outside of the therapy sessions.

Many of the neurological disorders that may be treated with the behavioral treatment method and apparatus have symptoms that cause a patient to perceive that he is performing a task (e.g., saying a phrase) at a sufficient amplitude (e.g., loud enough for someone to hear him) when in fact he is not performing the task at a sufficient amplitude. Therefore, a component of the behavioral treatment method and apparatus is calibrating the patient's perception of amplitude of his performance to the actual amplitude.

A therapist may stress calibration throughout the therapy session, including while interacting with the patient between tasks, a technique that may be called embedded calibration. The therapist may use embedded calibration techniques to train the patient to adopt the lessons learned into every performance, including the patient's interactions with the therapist. These embedded calibration techniques may be employed outside of a known therapy task or in an offhanded manner by the therapist. For example, the therapist may embed calibration techniques into the therapy by asking a question (e.g., "How did that feel?") after a therapy task is performed by the patient in such a way that the patient does not recognize that the question is asking the patient to perform a second task, in this case the task of answering the question.

The components of the behavioral treatment method and apparatus outlined above may be combined to create a therapy program in a number of ways. There are also many benefits that may be realized in a therapy program through combining several of the components outlined above into a single therapy program. For example, some of the benefits of the first group of tasks which focus on amplitude maximization include physical strengthening, aerobic conditioning, and range of motion. The benefits of these tasks support the performance of more complex tasks, such as the second group of tasks outlined above. Specifically, a therapist may leverage the fundamental skills practiced in the simpler skills with a patient's intuitive understanding of the complex skills (because the complex skills are derived from the skills suggested by the client and/or are "everyday" skills). In other words, the simpler skills of the first group focus on improving the qualities of the patient's performance (e.g., amplitude, pitch, quality, and/or motor control) and are highly successful, while the more complex skills are patient selected and use the patient's inherent understanding of the skill to allow the patient to integrate a successful movement into a more meaningful skill gradually. Through sequencing these fundamental tasks correctly, the therapist can allow a patient to practice complex skills with a high degree of success (i.e. high quality of performance) in a relatively short period of time. Through the immediacy and relevancy of these successful performances, the patient is continually motivated to adopt the techniques learned in the therapy sessions into every action the patient performs.

The practicing of complex skills, in itself, provides cross functional learning aspects of the therapy program. For example, the complex skill of remembering to add "Excuse me," before starting a sentence, actually saying that phrase in a loud and well-enunciated manner, and pausing after saying that phrase trains many more neural pathways and muscle systems than simple phonation exercises. Many of the neural pathways and muscle systems trained through the complex skills cannot easily or effectively be trained through skills that directly target those neural pathways or muscle systems in isolation. For example, vocal intonations, fine motor control and other subtle expressive features of human interaction can be both difficult to train and difficult to integrate into the patient's natural movement/performance, if they are not trained as part of a complex skill. Therefore, the present behavioral treatment method and apparatus provides tremendous distinct advantages because it is able to employ complex skills and introduce them early in the therapy program, while being simple to perform by the patient.

The uniqueness of the therapy is that by training a single motor goal—increased amplitude of movement (Big, Loud, Big and LOUD) the cognitive load is simple for the patient. The clinician (either speech or physical therapist) can indirectly integrate into the treatment additional communication or movement goals. For example, if treating a person who has had a stroke with motor speech disorders (soft voice, imprecise articulation) and language challenges (aphasia) these two foci can be addressed simultaneously in LOUD. The language goals are embedded into the hierarchy tasks. The explicit cue to the patient is to focus on LOUD but the hierarchy practice (not dysarthria word lists) includes language goal (syntactic structure).

Another cross-functional component of the therapy is how the intensity of the therapy program integrates continual focus on the fundamental skills, which force re-calibration of the patient's perception. This interaction allows the therapy program to act as an intervention within the course of the patient's neurological disease or as an ability to change motor behavior in patients who do not have a neural disease as opposed merely to supporting the functional skills against further skill degeneration by the neurological disease. Also, throughout the therapy program the intensity of the therapy schedule (e.g., number of sessions per week and number of skills per session) interacts with the complexity of the skills learned to provide a new paradigm for how the patient performs any task. By targeting both fundamental skills and quickly mastering a complex task (e.g., sometimes within the span of four weeks), a therapy program that combines these components may provide a patient with sufficient motivation, confidence and understanding of the fundamental skills required to apply those skills to any number of situations and/or tasks in the patient's life. Furthermore, many of the fundamental skills for one task type (e.g., speech) may be similarly applied to another task type (e.g., movement of limbs) and, therefore, the progress made in one task type often benefits another task type. In addition, these effects may be achieved in a short matter of time. Each of the components of the behavioral treatment method and apparatus distinguish themselves from those in a traditional therapy program that is designed for maintaining a patient's skills against degradation.

Figure 7:
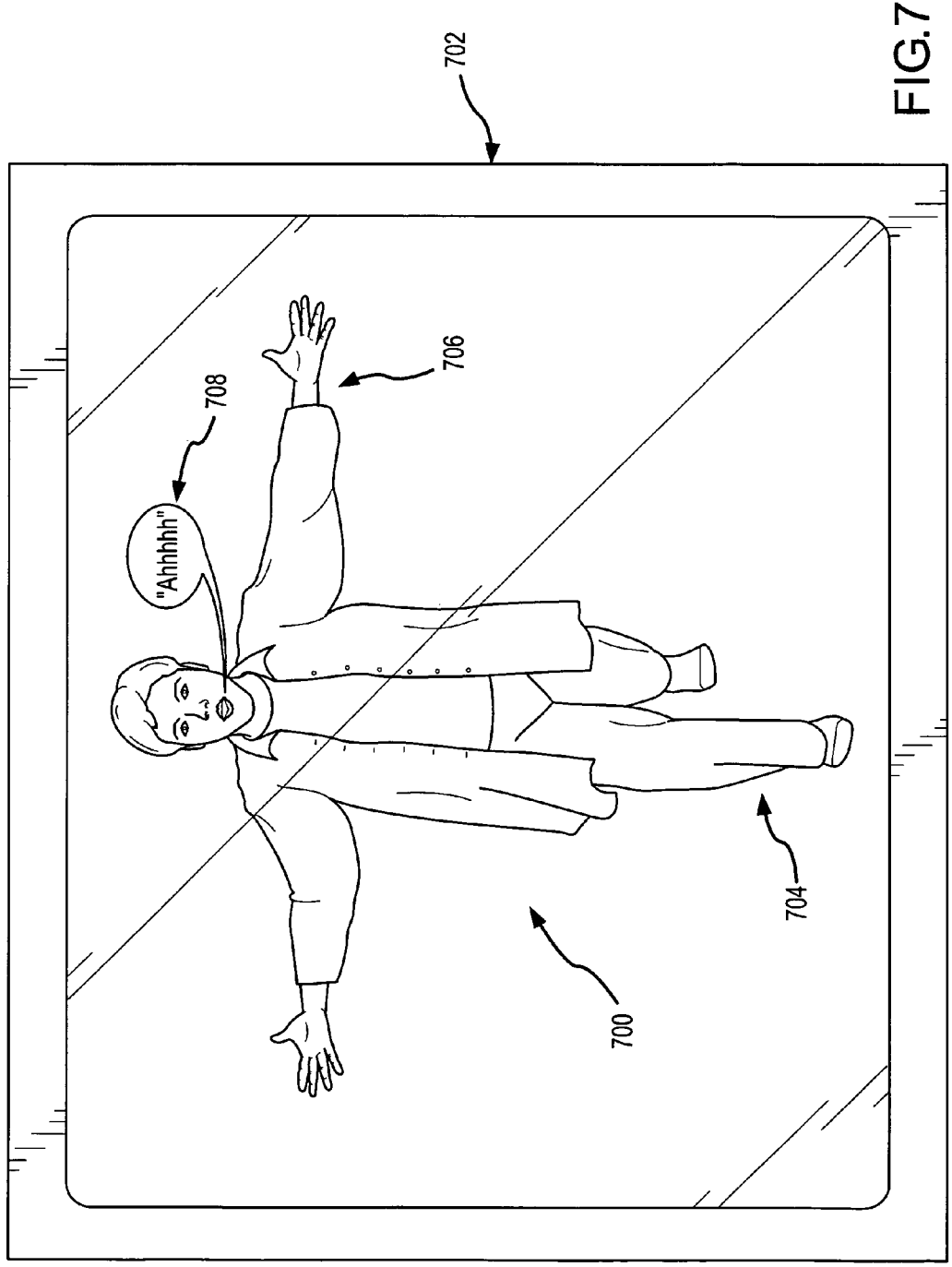
FIG. 7 is a depiction of a patient performing a fundamental combined movement and vocal skill.
Figure 8A:
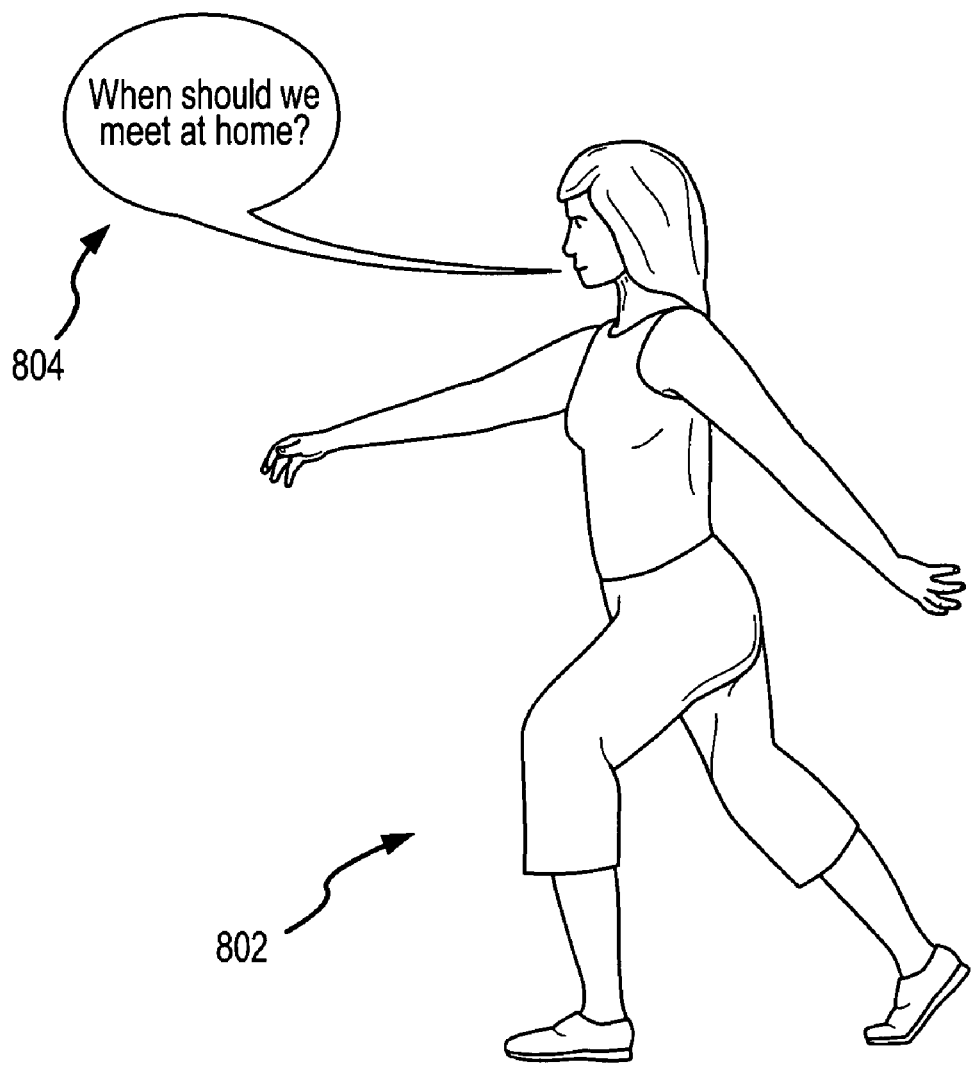
FIG. 8a is a depiction of a patient performing a complex combined movement and vocal skill, wherein the patient is walking across the room and stating a phrase.
Figure 8B:
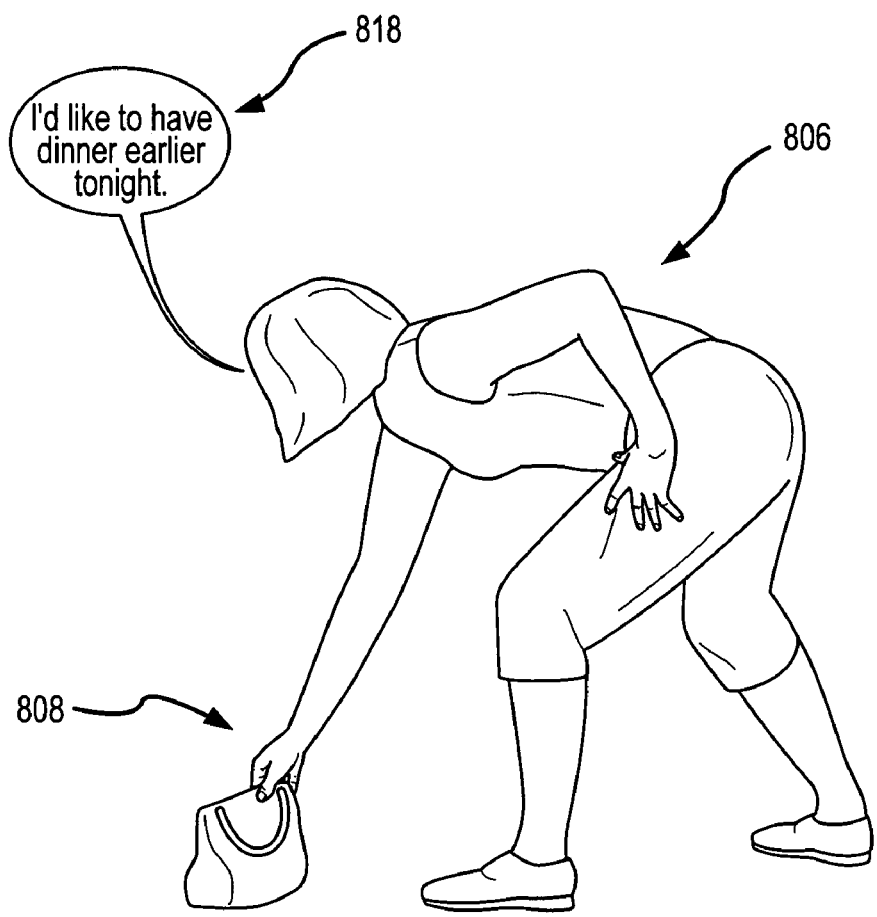
FIG. 8b is a depiction of the patient performing the complex combined movement and vocal skill, wherein the patient is bending over to pick up an object and stating a phrase.
Figure 8C:
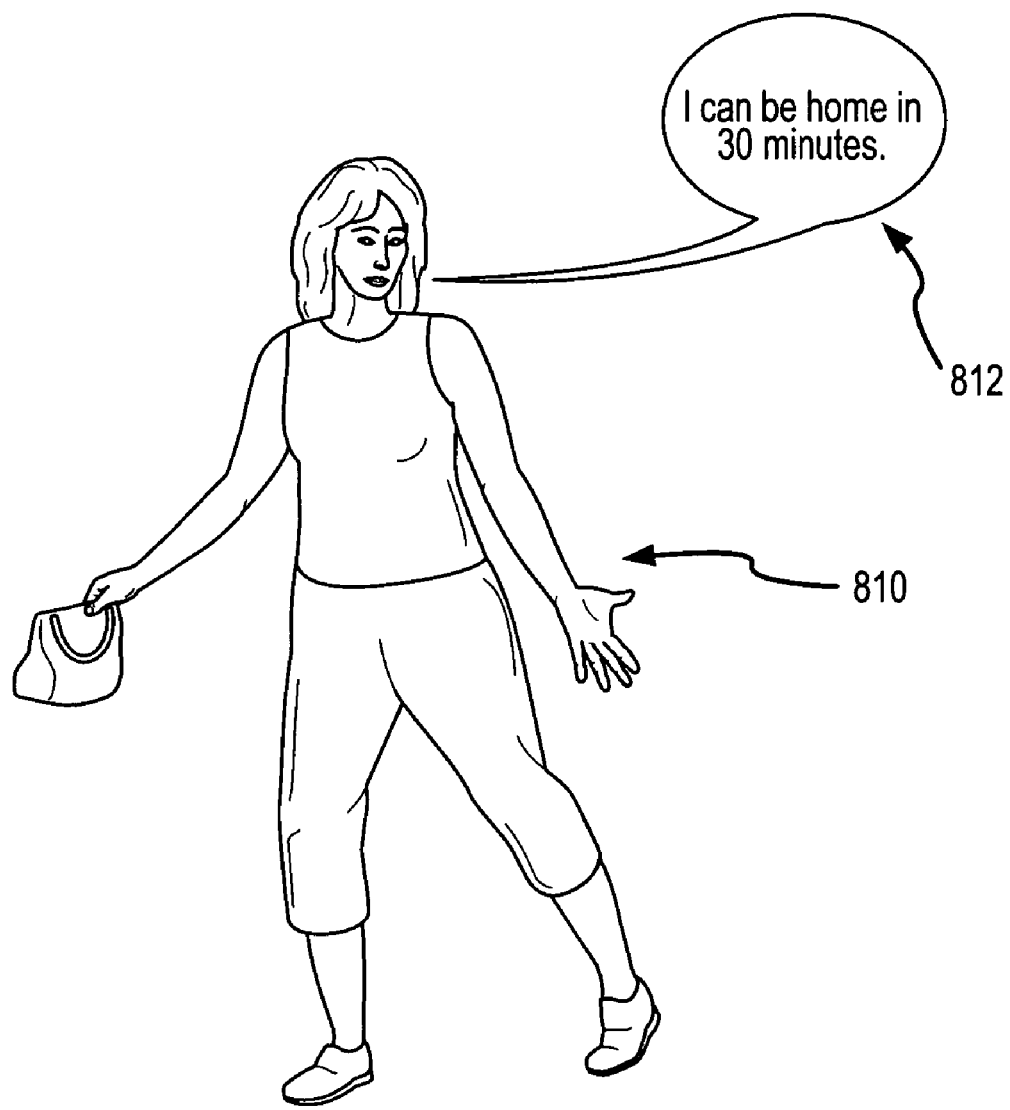
FIG. 8c is a depiction of the patient performing the complex combined movement and vocal skill, wherein the patient is turning around and stating a phrase.
Figure 8D:
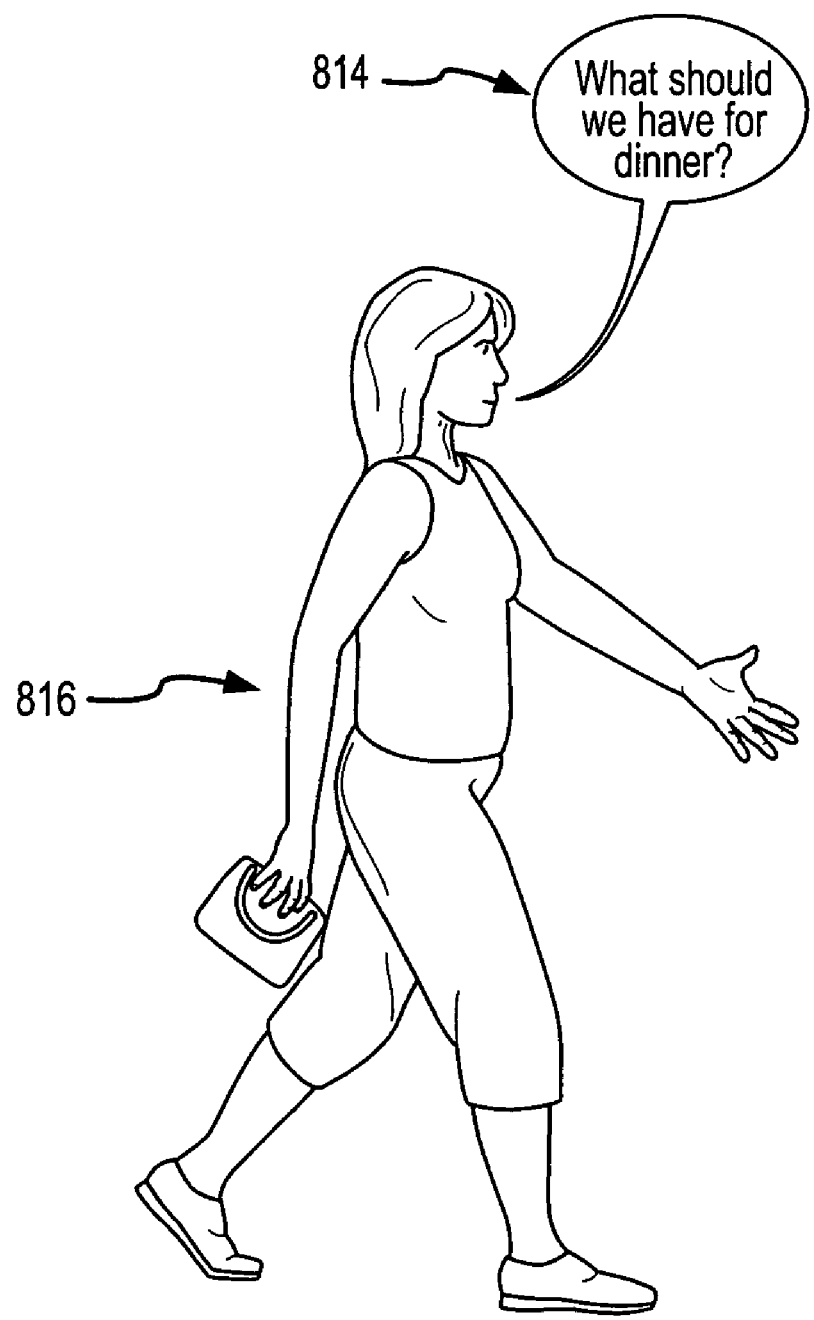
FIG. 8d is a depiction of the patient performing the complex combined movement and vocal skill, wherein the patient is walking back across the room and stating a phrase.
Figure 9:
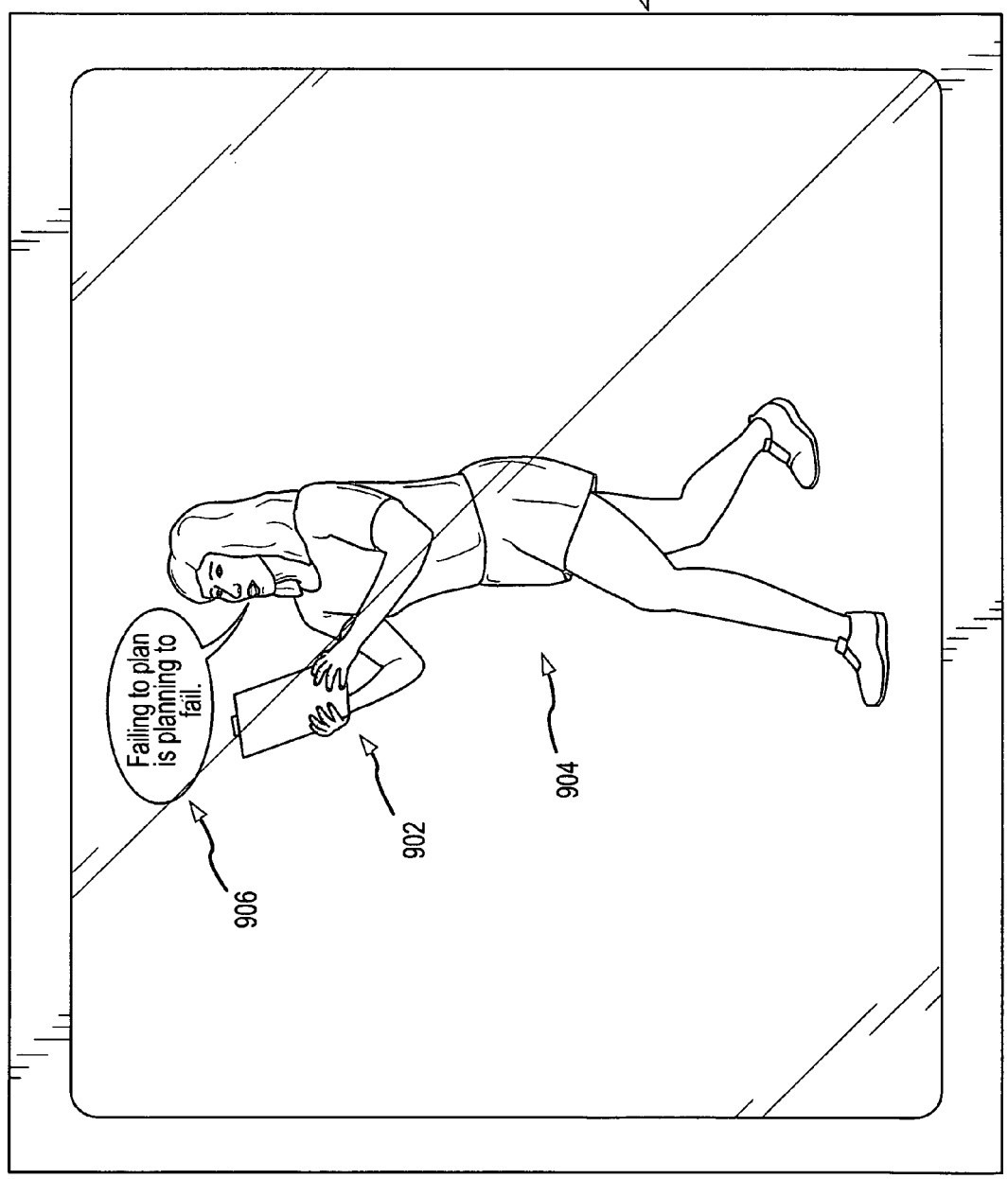
FIG. 9 is a depiction of a patient performing a complex combined movement and vocal skill, wherein the patient is walking with large-amplitude movements across the floor while holding a clipboard and reading phrases.

The therapy techniques may also combine big movements with loud speech into single tasks, as depicted in FIG. 7. A single task combining movements of limbs and speech may be simple in nature (e.g., stepping forward into a lunging position 704 with wide-open arms and hands 706 while making a loud "ahhhh" sound 708). A single combined task may also be complex by combining several speech elements (e.g., the elements contained in stating a phrase) with several movement elements (e.g., the elements contained in opening a door, including stepping to the side of the door as it opens). A cross-functional aspect of combining movements and speech tasks into a single combined task (whether it is a simple/ fundamental task or a complex task) is that a patient may learn how to emphasize amplitude in all of her efforts at once. Regardless of whether there is motor overflow, the patient may be able to find a more efficient way of performing the combined task.

The combination of therapy techniques allows for efficient learning and training during therapy program, and also allows cross-functional reinforcement of the lessons learned. For example, speech therapy with an emphasis on speaking louder than normal (e.g., greater than 70 dB SPL at 30 cm) can cause motor overflow in the form of extension movements of the body (e.g., arms, trunk) in some patients (e.g., patients with cerebral palsy). This is partially a result of the effort that is directed at speech systems "spreading" across to other systems, or motor overflow. Training both movements and speech simultaneously allows for reduction of motor overflow from the speech systems to other systems (e.g., limb movement systems) as well as from other systems to the speech systems. In addition, training both movements and speech simultaneously allows the patient to direct effort at both systems, and to reduce the motor overflow created in both systems simultaneously and more efficiently.

Training both movements and speech may involve integrating the movement in the speech in different ways. For example, movement and speech may be integrated starting on the first day of the therapy program, which may be called complete integration. The type of integration of therapy and speech therapy may be determined based on the severity of a patient's neurological disease and/or other diagnostic factors such as cognitive deficits or arthritic conditions, accent reduction, improving normal function.

The combined movement and speech therapy techniques described herein may only require a single therapist (e.g. a speech therapist or a physical therapist) to observe the patient performing a combined task. For example, a speech therapist may have the ability to observe a combined speech and movement task and to provide feedback on both parts of the task. The speech therapist's knowledge of the fundamental movement tasks (e.g., big movement of arms and legs) being practiced by the patient may contribute to the therapist's ability to provide feedback about the complex movement task (e.g., walking across a room). Also, both the patient's familiarity and the speech therapist's familiarity with the movement task help make the speech therapist's guidance sufficient. Another reason is that many of the complex tasks (e.g., speech, movement, or combined) are real world tasks that the patient wants to master. Furthermore, another reason is that these tasks may be repeated for several therapy sessions and built upon as the patient progresses. Therefore, a therapist with specialized training in speech may be able provide effective feedback after observing a combined speech and movement task. In this example, the next therapy session would be attended by a physical therapist who could also provide such feedback for the speech portion of the skills. In such an arrangement, each of the therapists will be able to provide more detailed guidance and instruction in their respective areas of expertise during the sessions in which they are present.

Figure 12:
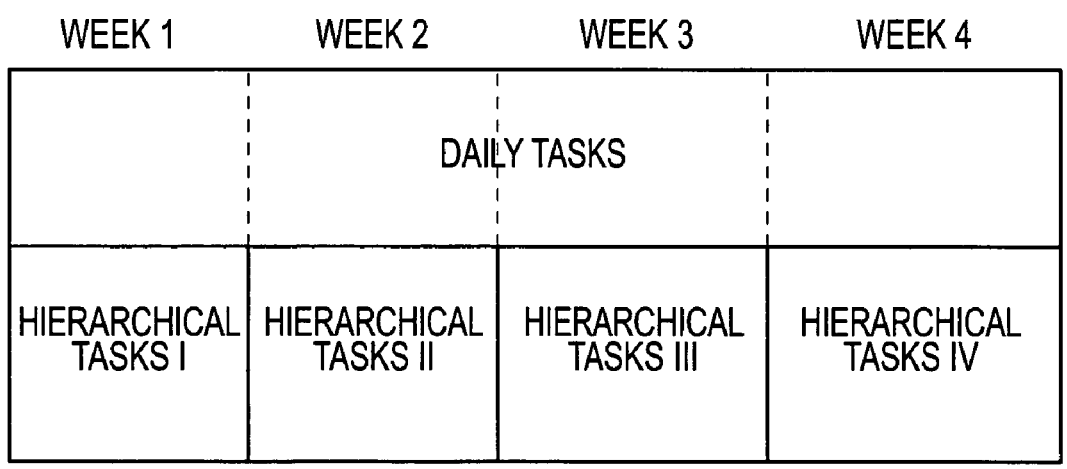
FIG. 12 is a depiction of the different components of the therapy technique that are utilized over the course of a 4-week combined speech and movement treatment program.

An exemplary treatment plan or program may include 16 sessions over four weeks, with four sessions per week, such as is shown in FIGS. 10, 11, and 12. FIG. 10 shows a treatment plan for speech therapy alone, FIG. 11 shows a treatment plan for physical (movement) therapy alone, and FIG. 12 shows a treatment plan for simultaneous speech and physical therapy. The daily tasks described include fundamental/simple tasks and complex (functional) tasks. These tasks do not change throughout the 16 sessions of treatment. The daily tasks are designed to rescale the amplitude of the motor output. The hierarchical tasks described below include hierarchical tasks (e.g., tasks that include many other tasks embedded in them, such as language or cognitive goals) and other complex tasks (e.g., complex tasks not contained by the functional tasks). The hierarchical tasks are designed to take the resealing achieved from the daily tasks and systematically train the patient in longer durations of speaking and moving and in more complex speaking/moving situations.

The exemplary speech therapy program shown in FIG. 10, including instructions for guiding a therapy session, includes:

Daily Tasks

The three daily tasks take up the first half (e.g., 30 minutes) of the treatment session. The three daily tasks include multiple repetitions with a focus on high effort and sensory calibration. These daily tasks never change throughout the 16 sessions of treatment.

Daily Task 1—Maximum Sustained Phonation (LOUD)

15 or more repetitions of maximum duration vowel sustained phonation while the therapist listens to the voice quality and tries to shape or stabilize the voice quality (e.g., a loud "ahhhhh" at a volume of 75-90 dB; or at an amplitude of at least 3 dB greater than prior to therapy); the therapist encourages longer duration and higher volume; the therapist may also ask the patient a question immediately afterward to teach calibration of the speech volume to the patient Daily Task 2—Maximum Fundamental Frequency Range 15 or more repetitions of highest pitch/tone 15 or more repetitions of lowest pitch/tone Daily Task 3—Maximum Functional Phrases Say 10 different functional phrases (they are pre-selected by the patient). These are phrases that the patient may normally say everyday in daily living, often multiple times per day. For example:

"Good morning" "Hello this is Mary" "Would you get the phone?" "Is it time for my pills?"

The second half of each session changes each week.

Week 1

The patient reads words, phrases of text using a LOUD voice

Week 2

The patient reads sentences using a LOUD voice

Week 3

The patient reads paragraphs using a LOUD voice

Week 4

The patient has a conversation using a LOUD voice

The exemplary physical therapy program shown in FIG. 11, including instructions for guiding a therapy session, includes:

Daily Tasks

The three daily tasks take up the first half (e.g., 30 minutes) of the treatment session. The daily tasks include multiple repetitions with a focus on high effort and sensory calibration. These daily tasks never change throughout the 16 sessions of treatment.

Daily Task 1—Sustained Bigness (Large Stretches) Tasks 8 or more seated repetitions of floor-to-ceiling stretch for at least 10 seconds; therapist works on increasing amplitude and duration 8 or more seated repetitions of side-to-side stretch, other details as described above Daily Task 2—Step and Reach Directional Tasks 10 or more big steps forward, reaching out to the side with both arms, hands opened, fingers and wrist extended 10 or more big steps backward, reaching both arms down and back, hands opened, fingers and wrist extended 10 or more big steps to the left, reaching out to the side with one arm on same side, hands opened, fingers and wrist extended 10 or more big steps to the right, reaching out to the side with one arm on same side, hands opened, fingers and wrist extended Daily Task 3—Rocking Tasks Rock back and forth 10 or more times, shifting weight without moving feet, with large swinging of the arms towards the ceiling Rock side to side 10 or more times, shifting weight without moving feet, with large swinging of the arms side to side Daily Task 4—Functional Movement Tasks Functional movement tasks are the same each session. The five functional tasks include: (1) sitting on a chair and moving from a seated position to a standing position 10 or more times while emphasizing large movements; (2) sitting on a chair and reaching side to side to the floor 10 or more times (while emphasizing large movements) to pick up an object; (3) standing and reaching up to grab an object 10 or more times (while emphasizing large movements); (4) standing and reaching down to grab an object 10 or more times (while emphasizing large movements); and (5) walking and then stopping to reach up or down to grab an object from a standing position 10 or more times (while emphasizing large movements).

The second half of each session includes hierarchical tasks that change each week. The hierarchical tasks vary each week as follows. First, the therapist interviews the patient to determine 10 tasks/things the patient would like to be able to do or do better. The therapist ranks the difficulty of these tasks and works on progressively harder tasks each week.

The exemplary speech and physical therapy program shown in FIG. 12, including instructions for guiding a therapy session, includes:

Daily Tasks

The three daily tasks take up the first half (e.g., 30 minutes) of the treatment session. The three daily tasks include multiple repetitions with a focus on high effort and sensory calibration. These daily tasks never change throughout the 16 sessions of treatment.

Daily Task 1—Maximum Sustained Phonation (Loud)/Stretch (BIG) Tasks 8 or more repetitions of the seated floor-to-ceiling task while sustaining loud "ah"

8 or more repetitions of the seated side-to-side task while sustaining loud "ah"

Daily Task 2—Maximum frequency (LOUD)/Directional (BIG) Tasks 16 or more repetitions of high pitch with big step and reach sideways, reaching out with both arms and hands opened and fingers maximally extended (alternate side to side)

8 or more repetitions of low pitch with big step and reach backwards, push arms down and behind as you bend over—hands opened and fingers maximally extended 8 or more repetitions of low pitch with big step and reach forward, reaching both arms open out to side, hands opened and fingers maximally extended Daily Task 3—Maximum Functional Phrases (Loud)/Movement (BIG) Tasks Pair each functional phrase (10 phrases) per functional movement, repeat each phrase with movement 5 or more times each session.

For example:

"Good morning" (LOUD phrase) with sit-to-stand (BIG movement)

"Hello this is Mary" (LOUD phase) with sit and reach (BIG movement)

"Would you get the phone?" (LOUD phrase) with stand and reach (BIG movement)

"Is it time for my pills?" (LOUD phrase) with walk and reach (BIG movement)

Week 1

The patient reads words, phrases of text using a LOUD voice. Simultaneously the patient is working on BIG posture and big movements.

Take a message (write down a number) while talking on the phone

Walk straight while answering questions

Week 2

Read sentences while standing at the chalk board and moving (march in place, step side to side)

Speak in sentences (spontaneous speech) while walking in the room (with and without obstacles on the floor)

Read sentences while reaching for objects (e.g., money) and placing it in cups. Switch back and forth between reaching and speaking tasks.

Read or speak in sentences while walking to objects (e.g., small balls), reaching big and picking them up and then pivot and walk to the other side of the room Read sentences while standing at the chalk board with repetitive movement tasks including marching in place with big arms, moving the arms reciprocally up with a reach, or side to side Reaching for small objects (e.g., money) with Big effort and putting into cups (flick money with BIG effort)—switching back and forth with reading sentences Walking around the room, picking up an object (large and small including money, paperclips, small to medium size balls) and a piece of paper, read the sentences on the paper LOUD, then place both the object and paper back on the floor BIG. Walk BIG to next paper and object and repeat Stand in place and march BIG (arms and legs) and read sentences Walk back in forth in room over and around obstacles (steps, noodles, etc.) while spontaneously speaking in sentences (e.g., name famous person and sentence or two about that person, general conversation questions)

Week 3

Reading paragraphs while standing moving

Reading while walking

Reading while reaching for objects

Reading while walk, pick up objects, pivot, walk

Reading while reaching for objects on counter

Reading while pulling out wallet, getting cell phoneGo and get your jacket and put it on, pick up your purse, and walk to open the door while telling someone "I had a good time . . . goodbye."

Answer your phone while standing, walk to go to a table to write down a message to yourself after hanging up.

Week 4

Talking while walking in a crowded hallway or room negotiating obstacles or people Talking while putting carrying dishes or laundry or coat/purse Talking while buying groceries in a store Talking while walking to car and getting in/out Talking while paying for groceries Talking while dressing (putting on/off shoes)

Talking while performing recreational activity (throwing, golf swing, tennis swing)

Talking while doing chores (sweeping, vacuuming, dusting, cleaning)

Reach to the floor pick up your purse or drink, stand up, walk to the table put it down or give it to someone and say "Can you take this for me?"

Get up from the table and ask someone "may I take your plate?" Carry dishes to the kitchen Walk to a car, unlock the door, get in the car while talking to the passenger Walk and turn different directions unpredictably while speaking (the therapist can turn unpredictably while the patient has to respond and keep talking)

As exemplified through the above example of a therapy plan, skill selection and sequencing are important to the therapeutic treatment method and apparatus described herein. The list of skills, groups of skills, and progression of skills may be modified by the therapist to the patient and/or the patient's particular symptoms. It is provided above as merely an example of a therapy plan and instructions.

As depicted in FIG. 1, a basic element of the therapy method and apparatus is a therapist guiding and supervising a skill performed by a patient. A therapist guides and supervises the patient through a therapy session which includes the patient performing several skills (e.g., 104), which may be repeated and refined (e.g., 110 and 112) several times. The skills may cause beneficial adaptations in the patient's brain (e.g., neuroplasticity effects). The therapist may guide the patient through the performance of a skill by demonstrating (e.g., 104 and 106) that skill to the patient. The therapist asks the patient to perform the same skill (102) and may also instruct the patient to focus on performing a part of the skill in a particular way (e.g., through refinement 110). The patient performs the skill and the therapist observes (108) the patient, noting particular elements on which the therapist would like to give feedback. These elements may include, for example, the stability of the patient's movement and a level of strain in the patient's voice. The therapist may then choose to ask the patient to repeat the skill (e.g., 110 or 112) and may offer an instruction for refining the skill (e.g., 110). The therapist may also choose to demonstrate a refinement of the skill for the patient 104. The therapy session may proceed in such a manner including multiple repetitions of the above steps which provide, among other things, guidance, observation, and feedback to the patient during the therapy session. The guidance or modeling is done primarily through action. In other words, the therapists simply says, "do what I do" versus the therapist explaining to a patient the changes in speech/movement desired.

The therapist may be present in the room with the patient, or may be at a remote location using technology, such as video conferencing technology, to interact with the patient. Examples of typical displays are depicted in FIGS. 2, 3, 7, and 9. The therapist may also be embodied by a recording of the therapist or a computer simulation designed to simulate the presence of a therapist through, for example, demonstrating skills for the patient, observing the patient performing the skills, and providing feedback to the patient. Use of technology will also be discussed more later.

The therapist performs the function of watching a skill 108 and selectively determining which skill to instruct the patient to perform next (e.g., 110, 112, and/or 114). After observing the patient's performance of a task, the therapist makes a decision whether to instruct the patient to perform the task again 112, to perform the task again with a refinement to the task 110, or to instruct the patient to perform another task 114. A decision to instruct the patient perform the task again 112 may be made because the patient did not understand the task as demonstrated or because the patient was unable to perform the task correctly. The therapist may therefore instruct the patient to perform the task again and give no further instruction 112, or refine the demonstration (e.g., 110, 102 and 104 in sequence) of the task through emphasis of a particular part of the task. Instructing the patient to perform the task again 112 and instructing the patient perform the task with a refinement 110 may reduce the deficiencies in how the patient performs the task. If there are sufficiently few deficiencies the therapist may decide to demonstrate another task and instruct the patient to perform that task.

The therapist also observes how well the patient performs. Deficiencies in how the patient performs the task such as aberrations in performance or failure to perform the task correctly may be interpreted by the therapist to be improper execution. They may also be interpreted by the therapist to be motor overflow. Therefore, the therapist may distinguish between different types of performance which are outside the normal range of the performance of the task. The therapist will likely ignore motor overflow, unless it is harmful to the patient or to the therapy goals, and will likely focus on refining improper execution so that the patient practices the task in a correct manner. The therapist thereby selectively "shapes" the patient's performance to the desired range of performance of the task in a specifically selective manner by allowing motor overflow to continue while modifying the guidance given to discourage improper execution.

Motor overflow includes effects such as increased tremor and increased dyskinesias, extension of upper extremities and trunk. Motor overflow will often subside in a patient as therapy progresses and, so long as it is not harmful to the patient, is a largely benign side effect of the patient's efforts to perform a task at a high level of effort. Motor overflow, therefore, is not viewed by the therapist as a negative treatment outcome. Attempting to reduce it can limit the positive effects of the behavioral treatment. Improper execution, in contrast to motor overflow, can include execution that is strained or pressed, such as vocal hyperfunction (e.g., stressed, strained or "strangled" voice) and/or stilted movement.

Shaping performance includes helping the patient to change the way they produce a loud voice, big movements, or the combination thereof. It may include, but is not limited to, varying posture, breath support, mouth opening, isometric exercise, pitch of voice, stance of the feet, and/or position of the hands. Shaping may include the therapist demonstrating or modeling the performance, and the patient then attempting to duplicate the demonstration by the therapist.

The therapist will continue to shape the patient's performance until the therapist determines that the performance is sufficiently free of improper execution to allow the therapy session to move on to stabilizing the correct performance of the task. The therapist will then instruct the patient to repeat the task correctly. The therapist will repeat this instruction a number of times, often with a minimum of 15 repetitions, and sometimes, for tasks with short durations (e.g., 5-7 seconds), as many as 20-25 repetitions or more. After the therapist is satisfied that the minimum number of repetitions has been performed and the correct performance of the task has been stabilized in the patient (e.g., it is successfully repeatable) the therapist may make the decision to instruct the patient to perform the next task (e.g. 112 and/or 114).

The decision to instruct the patient to perform the next task (e.g., 112 and/or 114) may be based on the stabilization of the present task and on a determination of how the next task may fit into the entire therapy program. For example, after a patient has stabilized the correct performance of a particular task the therapist may determine a subsequent task that is most appropriate given the state of the particular therapy session, the patient's performance thus far, and the goals of the therapy. The goals of the therapy may be set out by a patient and therapist for the session and the therapy program as a whole. For example, the therapist may advance from having a patient perform the fundamental task of vocalizing a sustained high-intensity vowel sound (e.g., a loud "ah") to having the patient perform the fundamental task of vocalizing a sustained high-intensity vowel sound and either a high or low pitch near the limits of the patient's range. Such transition may be performed as a matter of course, as is the case with some transitions between fundamental skills, or the transition between tasks (including the selection of the particular subsequent task) may be performed on the basis of the patient's performance thus far. For example, the patient may be interested in learning how to answer a phone, including the tasks of smoothly picking up the phone, placing it against her ear, and thereafter stating in a clear and un-strained voice "hello?" The therapist may use such input from the patient in determining a subsequent task and/or when a subsequent task is undertaken.

There are many skills that may be used in the therapy program. In the behavioral treatment there are at least two broad types of skills or tasks through which a patient may be guided. The first type of skill may be exemplified by the task of vocalizing a sustained high-intensity vowel sound (see generally FIGS. 2-4) or by the task of reaching across the patient's body with both palms open and with fingers stretched wide (see generally FIGS. 6a-6c). This first type of skill may be referred to as a fundamental skill or task, a maximum "bigness" skill or task, or a maximum fundamental frequency skill or task.

The second type of skill is a complex skill, generally depicted in FIGS. 8a-8d and FIG. 9. The second type of skill may be a combination of sounds such as walking across a room 802, reciting a phrase like "When should we meet at home?" 804 or a combination of the movement tasks such as bending over from a standing position 806, picking an object up 808, and standing up 810 while reciting another phrase 812, 814, or 818. The complex skill may include many elements including other phrases (e.g., 812, 814, and 818) or movements, such as walking back across the room 816. This second type of skill may be referred to as a functional skill or task, a carryover exercise, a maximum functional phrase or a complex skill or task. The second type of skill may be developed by the therapist based on, in the example of speech therapy, what a patient may want to learn to say well in a real-world situation, and also based on specific communication problems of the patient. For example, the patient may want to boldly but politely interject the phrase "Excuse me," before making a request. The inability to do so may be referred to as a pragmatic deficiency in the patient, and developing the pragmatic skills to overcome this deficiency may be a goal of practicing a complex skill or task.

A sub-type of complex skills may be described as a skill or task that comprises the practicing of another skill. For example, this sub-type of complex skills may include the incorporation of a smaller task, such as holding an object steady, into other tasks throughout the therapy session and/or program. For example, in FIG. 9, a screen 900 shows a patient holding an object steady 902 may be incorporated into the task of walking across a room 904, turning to face someone and/or saying a phrase (e.g., 906) to them. This sub-type of complex skills may be referred to as hierarchical skills, endurance tasks, covert tasks or implicit skills. There are many ways for therapist to create a hierarchical/implicit skill to covertly test how the endurance of a patient's mastery of a fundamental skill. For example, a therapist may embed a fundamental task into a complex skill by guiding the patient through stating a functional phrase while also implicitly guiding the patient to maximize his perceived amplitude. A therapist may also covertly place alliterations into a paragraph that the patient must read while opening a can of soup, thereby reinforcing a phonological skill while practicing a motor control task. Another example includes having the patient perform a routine task that the patient performs commonly outside of the therapy session. The therapist can then observe the patient perform that task and see to what extent the patient incorporates the fundamental skills into the task. For example, the therapist may ask the patient to give a lecture the patient gives regularly. Through many of these techniques, the therapist can reinforce the use of a skill beyond the time when the patient practices it explicitly. In the manner described above, the therapist can simultaneously train amplitude/loudness while addressing language deficits such as semantic, syntactic, and phonological problems. In particular, this may be relevant to aphasia and pediatric patients. While the therapist is addressing a range of sub-tasks and goals (e.g., pragmatic skills, complex tasks, language goals) the explicit goal for the patient always remains simple, that is, it is focused on single motor control parameter of increased effort and amplitude of movement (Loud, Big).

Simple skills, or skills in the first group of skills or tasks, may be effectively combined with complex and hierarchical skills, in part because fundamental skills may continue to train a patient even after he has "mastered" them. For example, a patient who has mastered the skill of vocalizing a high-intensity vowel sound 400 may continue to practice the underlying skill (e.g., the more fundamental skill) of questioning and testing his perceived level of effort (represented by the arrows 302 and 408) by continuing to practice the same skill even though he has already "mastered" it. This is a result of this skill being designed to have a goal that is a "moving target" for the patient. For example, a high-intensity vowel sound 400 produced near the top of a patient's range, though it may sound different as the patient improves in ability, remains an effective technique in producing neuroplastic benefits in the patient throughout the therapy. Furthermore, a patient will begin to calibrate his perception of his effort (302 and 402) with his realized sound (or movement), and thereby internalize and adjust for any differences he may have between reality and his perception. As the patient improves as a result of the neuroplastic benefits of this therapy method, practicing a fundamental skills such as a high-intensity vowel sound 400 both seems less loud to the patient (e.g., because his perception and the reality of his performance are less different) and becomes physically easier for the patient (e.g., because the muscles and neural pathways to those muscles have been strengthened). Therefore, the behavioral treatment method and apparatus includes repetition of fundamental skills and tasks, both alone and in combination with complex and hierarchical tasks, throughout the therapy program. For example, an hour-long speech therapy session may begin with 30 minutes of fundamental skill practice (e.g., sustained high-intensity vowel vocalization and a pitch near the top of the patient's range). Furthermore each therapy session of the therapy program may include the same 30 minutes of fundamental skill practice, including potentially the same or substantially similar fundamental skills, throughout the entire therapy program.

Figure 5:
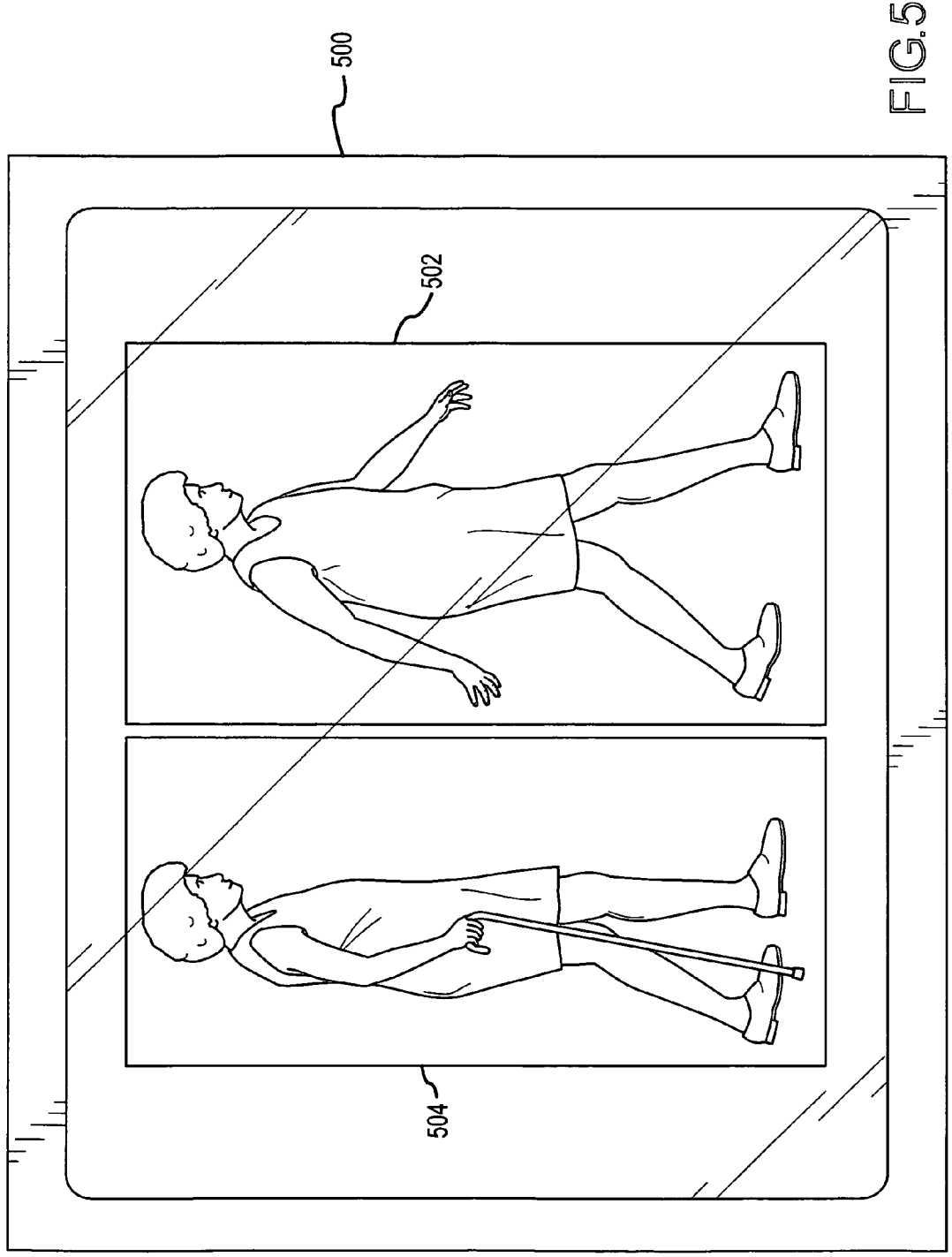
FIG. 5 is a split screen display comparing two performances of a fundamental movement skill, at different amplitude levels.

There are also fundamental skills relating to movement, such as depicted in FIGS. 5, 6a-6c, and 7. FIG. 5 shows a patient viewed in a split screen display. Either one of the representations 502 and 504 may be recorded or displayed in real-time. In both representations 502 and 504 the patient may feel as if she is moving with big movements, depending on how her perception matches with the reality of her movements. Representations 502 and 504 may be used to show a patient her progress from the beginning size of her steps as shown in representation 504 to a much larger size as shown in representation 502. The side-by-side representations 502 and 504 may be also used to calibrate a patient's perception of her movements. A therapist may show a patient that what feels like a big step to her may actually look like a small step reality, such as in representation 504. Fundamental skills such as taking a "big step" and therefore offer patients great insight into their symptoms, the progress of their therapy, and/or the desired amplitude of the fundamental skill they are trying to perform. A split screen format 500 can also be beneficial as a therapy aide.

Figure 6A:
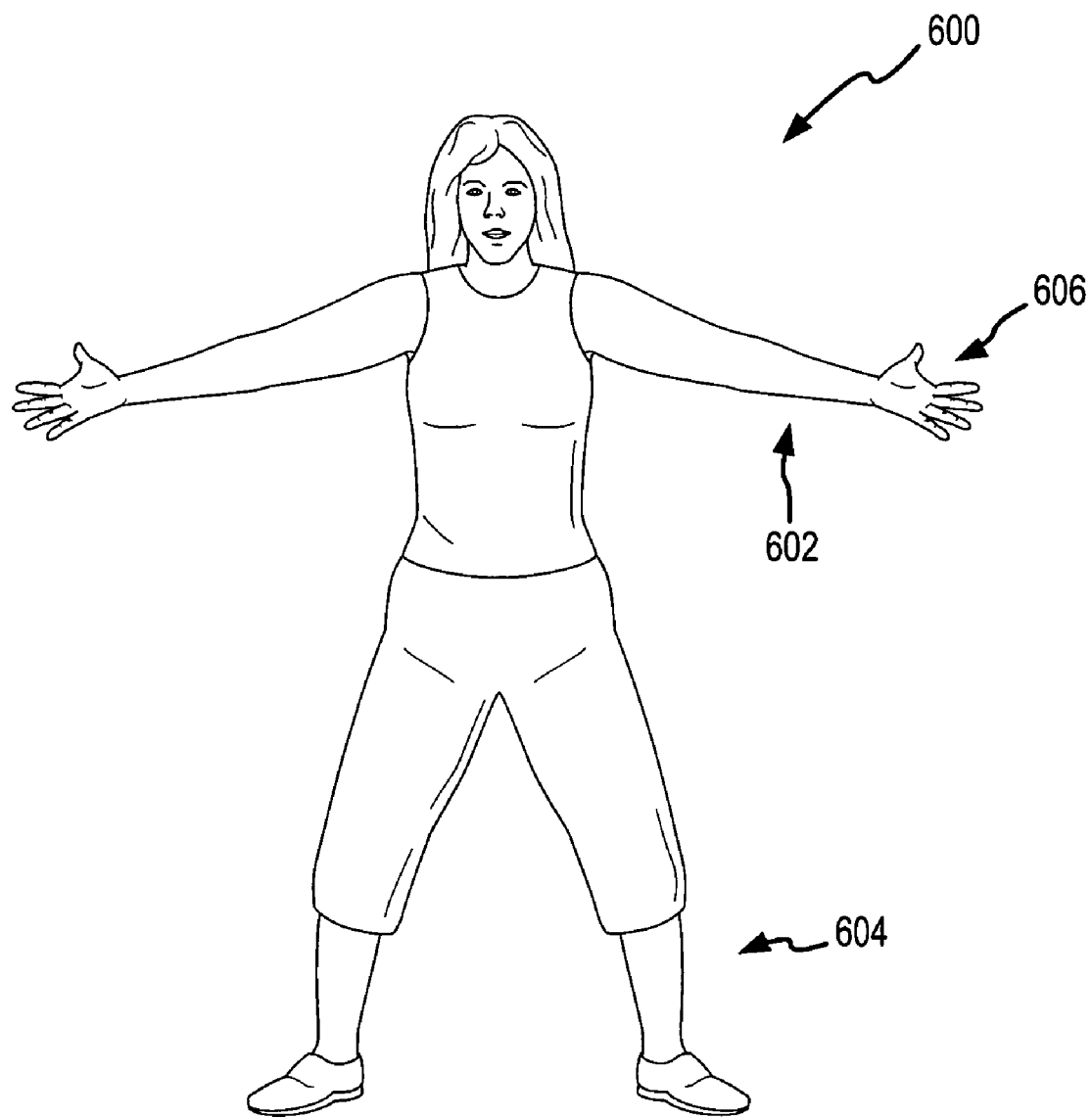
FIG. 6a is a depiction of a patient performing a fundamental movement skill with the patient in a starting position.
Figure 6B:
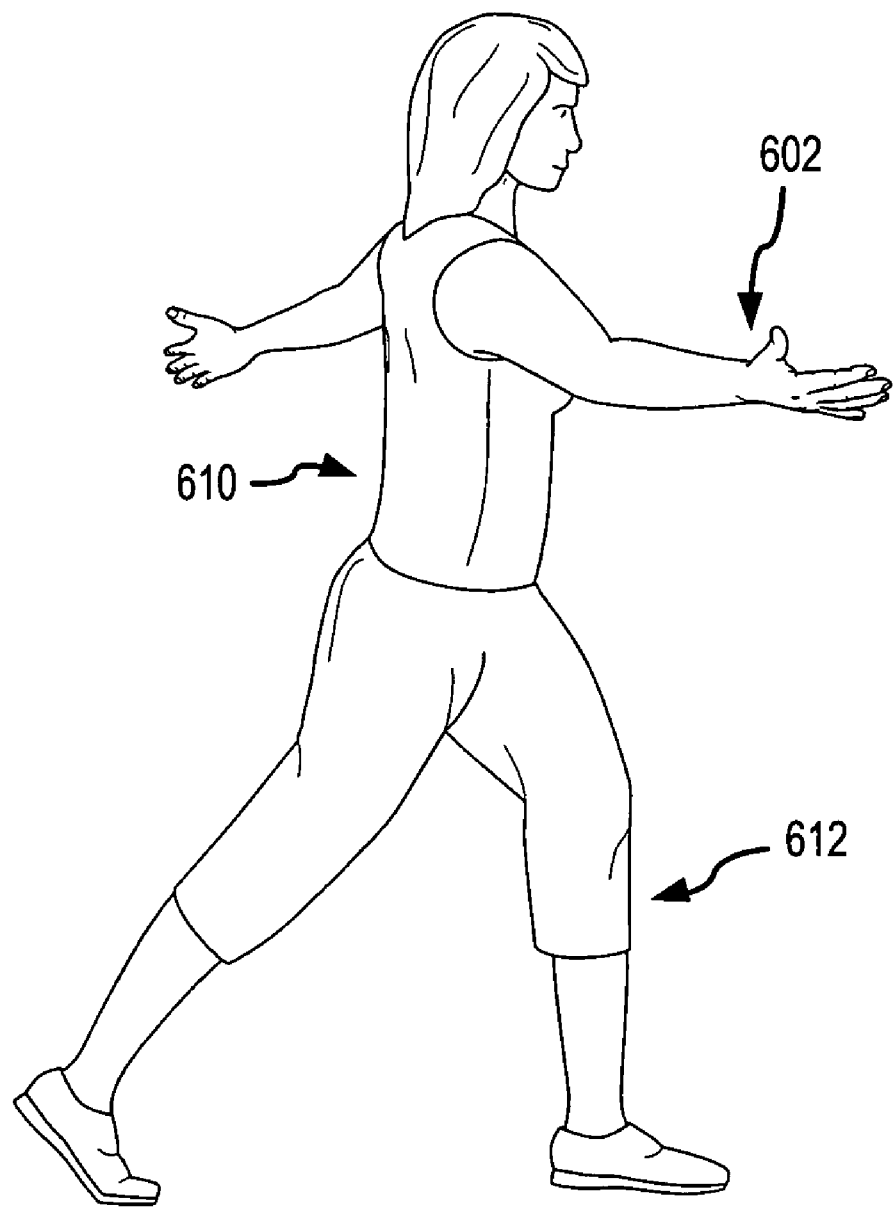
FIG. 6b is a depiction of the patient performing the fundamental movement skill with the patient part of the way through the skill.
Figure 6C:
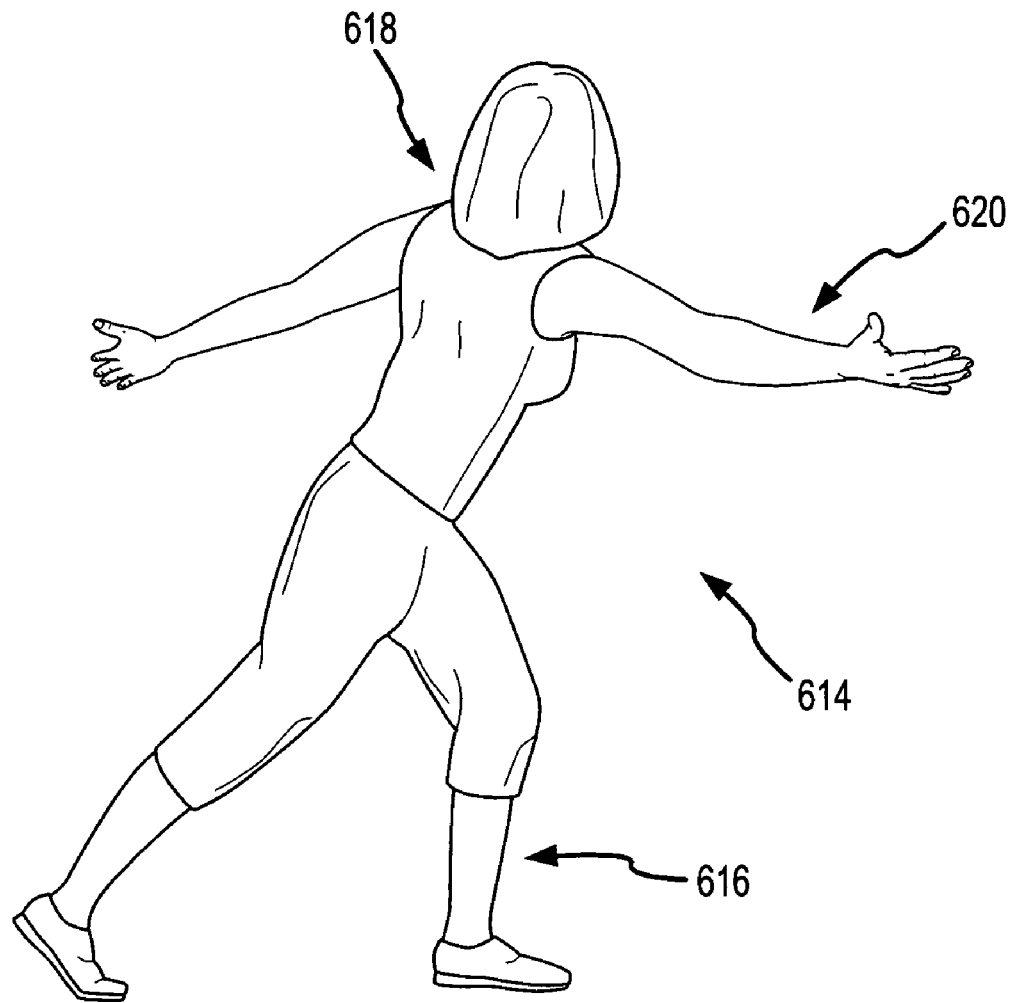
FIG. 6c is a depiction of the patient performing the fundamental movement skill with the patient in the finished position.

Other exemplary fundamental skills relating to movement are depicted in FIGS. 6a-6c. FIG. 6a shows a patient in a "big" starting position 600 for a fundamental movement skill. Her arms are stretched open wide 602, and her feet are spread forming a wide stance 604. The therapist may have to convince the patient that she can stand with their feet so wide apart 604 and her arms so wide open 602. The therapist should also instruct the patient to keep her hands 606 stretched as wide open as possible. This type of extension may be uncomfortable for the patient, but may help achieve many of the therapeutic benefits of this fundamental skill. FIG. 6b shows the patient continuing to hold her arms stretched open wide 602 while she rotates her torso 610 to her left. Because of her wide stance 604 her hips rotate, and she puts weight on her left leg 612. FIG. 6c shows the patient in the extended finished position of the fundamental movement skill 614. Much of her weight is on her left leg which is in the lunging position 616. Her head and shoulders 618 face almost opposite the direction they faced when she began the skill, and her arms and hands are still in an extended position 620.

Fundamental skills may also be combined movement and speech skills such as the example shown in FIG. 7. FIG. 7 also shows the fundamental skill 700 being displayed on a screen 702. The fundamental skill 700 includes a combination of fundamental skills: a big step or lunge 704; stretching the arms wide with palms open 706; and saying a loud sustained vocal sound 708, such as "Ahhhhhh." Combining fundamental skills with other fundamental skills does not necessarily make the combined skill (e.g., 700) a complex skill. Each of the component fundamental skills may require only a simple movement or vocalization to be performed with a large amplitude, and combining them does not increase each component's complexity.

Fundamental skills may also be combined with complex skills. The behavioral treatment method and apparatus allows the therapist to flexibly interleave and embed fundamental skills throughout any complex or hierarchical skills. By doing so, the therapist can provide the patient with more opportunity to practice the fundamental skills as well as an opportunity to practice the skills in the context of a more complicated skill. The patient, therefore, must focus on the fundamental skill (e.g., moving with large, smooth, "big" movements) while also focusing on performing the complex skill (e.g., walking across a room in while stepping onto and off of boxes). This tests the patient's ability to perform the fundamental skill under more stressful situations and situations applicable outside of the therapy session. Furthermore, as the patient internalizes the fundamental skill, it becomes a habit and no longer needs to be intentionally practiced. The patient thereby is able to focus only on performing the complex skill.

Of course, the therapist monitors the patient while he performs the complex skill in the therapy session to ensure that the patient is continuing to exhibit outward signs of the fundamental skill regardless of the patient's level of internalization of the fundamental skill as a habit. This internalization of the skill may also be understood as successful recalibration of the patient's perception. Thus, even though the patient may not feel as though his movements and speech are not as "big" or "loud" as they once seemed, the patient will be able to correctly perceive and adjust his actions in real-world situations. In other words, it is not the case that the patient, having trained with loud speech or big movements in the therapy sessions, will perceive that performing at those intensities or amplitudes is normal. The correct calibration of the patient's perception (e.g., his brain function) will allow the patient to correctly perceive and adjust the amplitude of his actions in real settings and everyday situations outside of the therapy sessions.

Everyday situations often include complex tasks with many different parts to them such as, opening a door to walk into a room, stepping into the room, closing the door, and sitting down in a chair. Each of the parts of a complex task may be understood by the patient and may be performed in combination by the therapist guiding the patient to perform the complex task as opposed to the individual parts in isolation. For example, a patient may already understand exactly how to walk across a room, pick something up, and walk back. The therapist may ask the patient to do that complex task with big movements (with a large amplitude) early in the therapeutic process, so long as the patient has already practiced the fundamental skills of moving with big movements. The complex task is thereby enabled through the patient practicing, understanding, and mastering the fundamental skill (i.e., larger amplitude movement). Additionally, as noted above, practicing the complex skill continues to practice of the fundamental skill and reinforces its use in all situations. Thus, the attention in therapy remains "simple" for the patient in that he/she only has to focus on large amplitude movements (Loud, Big, or Big and Loud) and not the sub-components of accomplishing complex movements.

Hierarchical tasks provide opportunities to practice fundamental skills and skills specific to a particular patient's symptoms. For example, if a patient has trouble remembering to make questions sound like questions (such as through a rising vocal inflection at the end of a sentence), the therapist may guide to patient through an exercise that requires the patient to move around a room using big movements and asking questions in a loud voice. The clinician will model the change in inflection for asking questions, but the explicit cue to the patient will always remain speak loudly. Thus, the clinician is able to indirectly change patient behavior (changes in inflection) through a model while the patient maintains a simple, single focus on amplitude of movement. This type of modeling to change behavior is novel and unique in speech and physical therapy programs. In another example, the complex skill practiced by the patient can include having a free-form conversation in a loud voice with the therapist while walking about a room, stepping over things, and picking up objects, all with big movements. The therapist may include in the conversation (e.g., hierarchically embed in the conversation) many opportunities for the patient to ask questions. Hierarchical tasks are, therefore, useful to the therapist in training the patient on multiple levels through one task. The therapist can design a hierarchical task to fit the patient's therapeutic needs as well as her desires for greater functioning in her life.

Complex tasks are often the most useful for patients to learn during a therapy session because they likely can be used in the patient's life similar to the way they were practiced. The therapist may gain a sense of what might be useful in the patient's life through interviewing the patient before and during the therapy program to learn about the patient's life, such as her interests, activities, difficulties, and areas in which she would like to see improvement. Complex skills can include conversational phrases, linking a phrase with an action, or in series, walking, bending over and then picking something up (see FIGS. 8a-d). The therapist may use complex tasks because they provide the reward of being directly useful in the patient's life. Complex skills are, therefore, often more directly relevant to a patient than fundamental skills, and can effectively be used by the therapist as a motivating tool. The complex skills are trained to take the resealed amplitude of movement achieved during fundamental skill training and carry them over to everyday tasks. Thus, the fundamental skills become a part of how the patient speaks and moves in daily living. This allows for continuous practice of fundamental skills (i.e., beyond the practice of sustained "ahs" and big stretches) and increases likelihood of generalization of fundamental skills to all aspects of daily living. The therapy sessions guided by the therapist may be part of an overall therapy program or plan. For example, a therapist may outline a therapy program in which there are four 1-hour sessions a week for four weeks, or a total of 16 sessions in about a month. The behavioral treatment method and apparatus may include a more rigorous scheduling of sessions than other methods of therapy. An intensive schedule such as this can interact with the intense repetition of fundamental skills within each session, the quick introduction of complex skills into the therapy, and the relevancy of those complex skills (via the patient suggesting them), to create an intense, challenging, but extremely rewarding overall therapy program for the patient. For example, if a therapy session includes 30 minutes of fundamental skills, four times a week, the patient will practice two hours of fundamental skills during the first week of the program. The therapist may continue to monitor the use of the fundamental skills even between skills through embedded calibration techniques, guiding the patient to focus on those skills nearly constantly. Considering also that the complex skills learned in that week also include practice of the fundamental skills, the patient will be required to focus on the fundamental skills for four hours during the first week. By the end of four weeks the patient has spent 16 hours focusing on the performance of fundamental skills in isolation, as embedded by the therapist throughout the session, and in the context of doing hierarchical skills and complex skills. By the end of four weeks time, the patient is sometimes able to incorporate the fundamental skills into spontaneous tasks such as freeform conversations or movements that do not need to be thought about beforehand. Therefore, an intensive therapy program can provide an intervention in a patient's life. Furthermore, this intervention can have lasting effects because the fundamental skills may be adopted by the patient as habits and used spontaneously outside of the therapy sessions.

The therapy program, however, need not be limited to an intervention. The therapy program may be designed for maintenance (e.g., ongoing therapy), intervention, or a combination thereof depending on the particular disease, symptoms, or goals of the patient. For example, a patient with Down syndrome may require at least a portion of the therapy program to be focused on maintenance or ongoing therapy. It should be understood, however, that maintenance therapy does not necessarily coincide with a therapy goal of maintaining a particular level of functioning. For example, positive progress in a patient's level of functioning may be achieved through a low-level or maintenance level therapy program.

Sometimes scheduling an intensive therapy program is difficult. Even maintenance level therapy programs may be difficult to schedule, such as in situations where the therapist or patient is busy. In situations where an intensive therapy program schedule (or some other reason) makes a virtual therapy session helpful or convenient for the patient or the therapist, interactive technology may be used to conduct a therapy session remotely. Interactive technology is one example of an apparatus in that may be used in a remote or virtual therapy session. For example, a camera may be linked over the Internet with a display screen, allowing a patient's movements to be observed by a therapist. Examples of these screens are the split screens in FIGS. 2 and 5 and the display screens in FIGS. 7 and 9. Another example of interactive technology includes a microphone interconnected over the Internet with a speaker allowing a patient to hear examples of a vocal skill as performed by a therapist. Interactive therapy technologies need not be connected in real-time. A therapist's examples and a patient's performances may be recorded and observed at different times and in different places. One example of this may include a therapist mailing a patient a recording of examples and the patient providing back to the therapist a recording of her performances. Another example of this is a computer simulation that uses recorded examples and provides feedback based on observed patient performances (e.g., through image capture and image correlation technologies). Indeed, as discussed herein, a therapist may include any simulation or analogue of a therapist.

Interactive technologies may also be used in a therapy session where the therapist is present. For example, a therapist may use a split screen display (e.g., 500) to show a patient a real-time recording of the patient's movement (e.g., 502) alongside a previous recording of the patient's movement (e.g., 504). The patient's movement in real-time may also be displayed alongside a recording of the therapist demonstrating an example. Another example may include the therapist playing back a tape recording of the patient performing a particular vocal task earlier in the therapy. The therapist may then record the patient performing the same task and play for the patient both recordings. This method and apparatus may be used to help the patient understand the task or the therapist's feedback without having to interpret complex instructions from the therapist. Further aspects of using these tools to demonstrate therapeutic tasks are also discussed above.

Figure 13A:
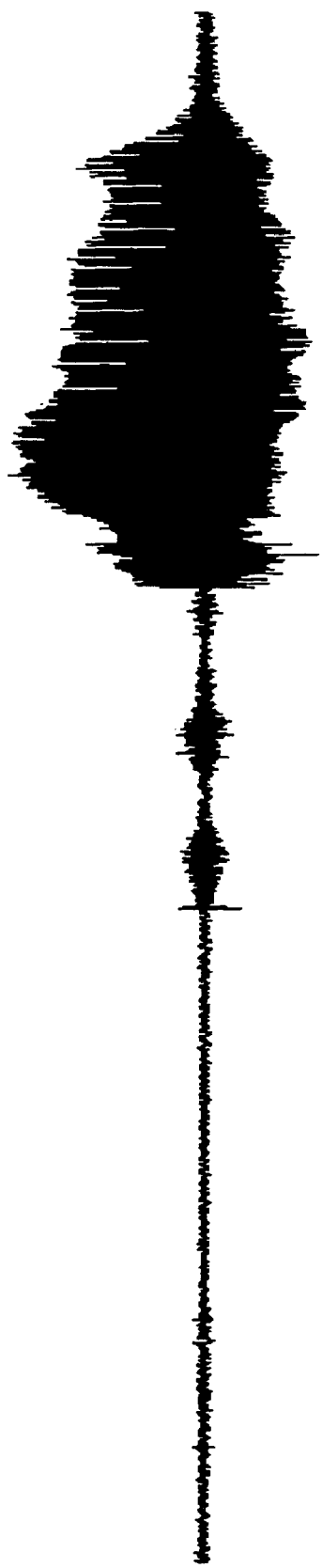
FIGS. 13a and 13b are signal traces of the audio volume level recorded during an identical vocalization exercise, before and after treatment methods have been applied.
Figure 13B:
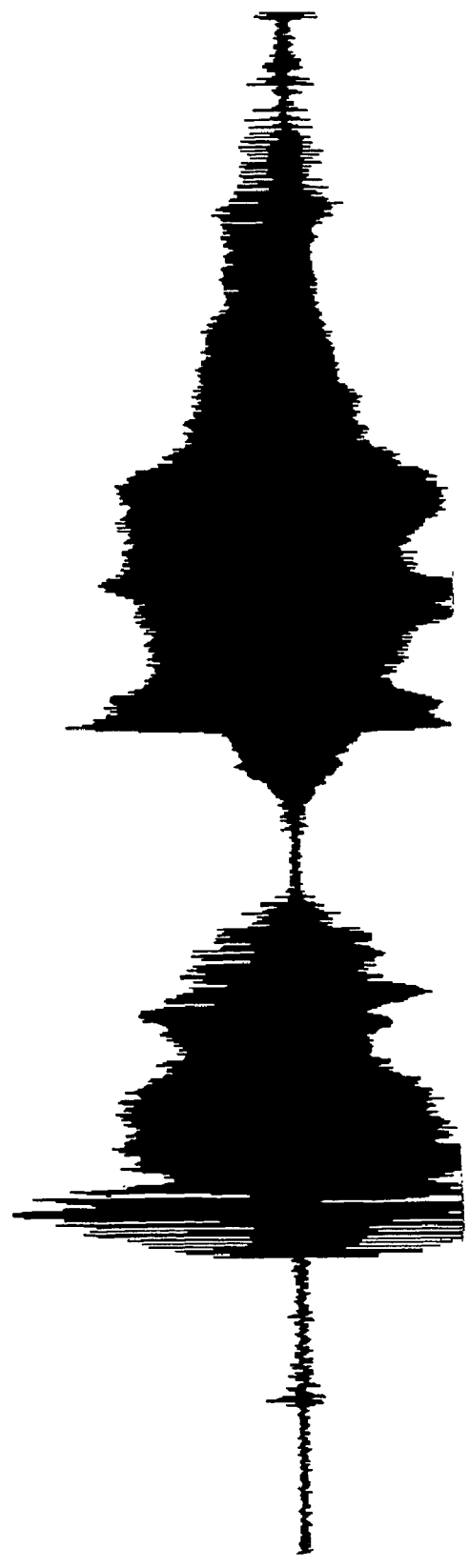

FIGS. 13a and 13b illustrate the difference in volume level as represented by an audio signal recorded of a patient saying the phrase "I don't know" before therapy per the present invention (FIG. 13a) and after therapy per the present invention (FIG. 13b). As can be seen, the amplitude of the sound from the patient has increased dramatically.

Figure 14:
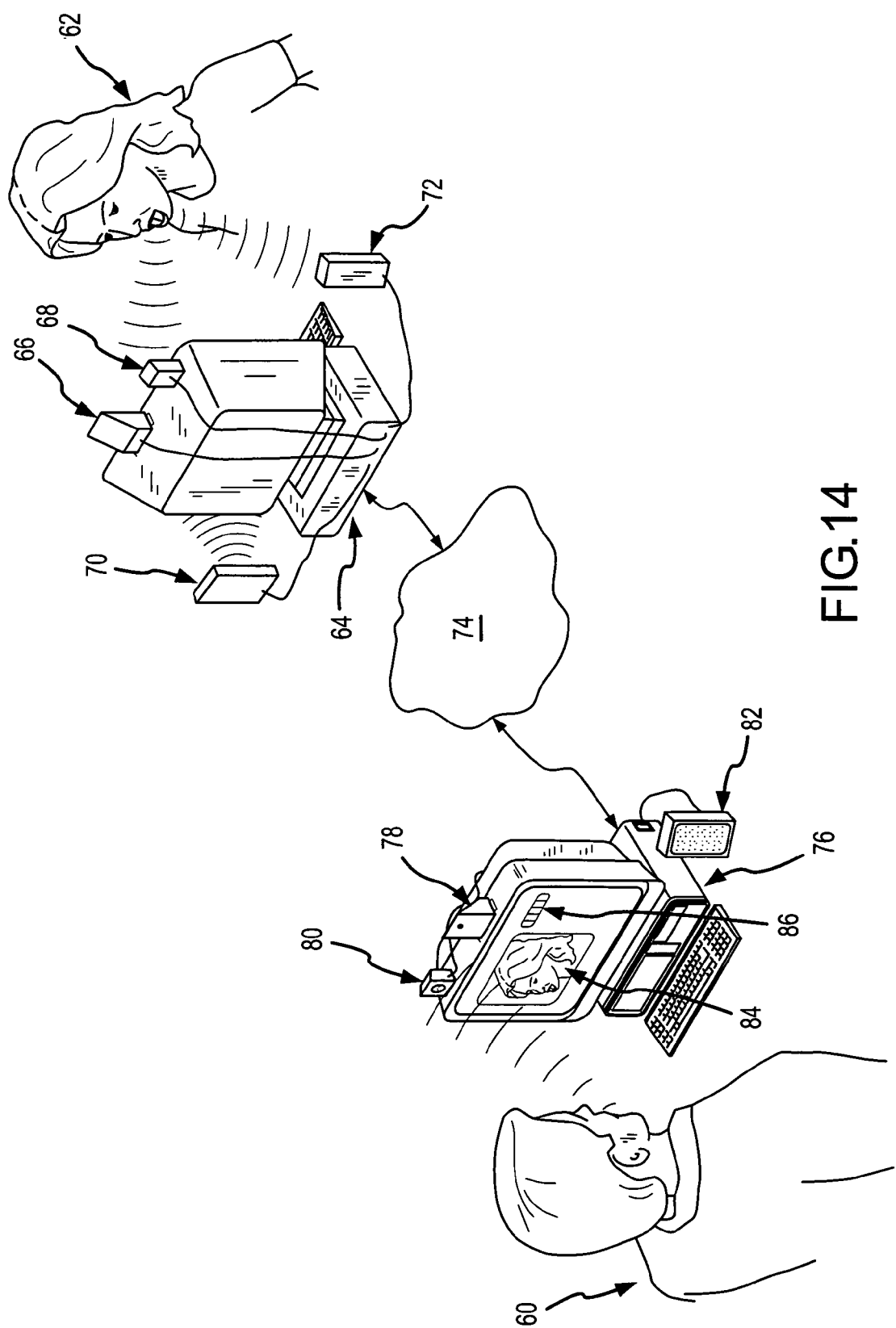
FIG. 14 is a depiction of a patient performing a vocal skill, and apparatus for capturing images and audio of the patient as well as measuring the volume of the patient's audio and providing this information to the therapist.

FIG. 14 shows a therapist 60 providing therapy to a patient 62 from a location remote to the patient 62. The patient 62 is near a personal computer 64, having a web cam 66, a microphone 68, a loudspeaker 70, and a sound pressure level meter 72 attached thereto. The patient's computer 64 is attached through a data network 74, such as the Internet, to a personal computer 76 near the therapist 60. The therapist's personal computer 76 may also have a web cam 78, a microphone 80, and a loudspeaker 82 attached thereto. After the therapist's instructions are passed to the patient 62, the patient performs the requested task (e.g., vocalization of "ahhhh"). The therapist 60 is able to see an image 84 of the patient on the display of her computer 76 and hear the patient through the loudspeaker 82. In addition, an indication 86 of the sound pressure level measured by the meter 72 is displayed on the therapist's computer 76. Alternatively, the meter 72 could be eliminated and the microphone 68 and computer 64 could be used to calculate the sound pressure level. It may be desirable to place the meter 72 or microphone 68 at a specified distance (e.g., 1 meter) from the patient.

The therapy programs described herein provide many benefits and advantages to a patient. The patient benefits from using a greater amplitude (e.g., louder voice, bigger movements) than is normally used in therapy through strengthening the muscles and brain systems supporting the performance of a task. The patient may experience motor overflow such as extension of arms and trunk movements when he tries to talk in a louder voice than is comfortable. However, this motor overflow often subsides in a patient as the patient's body and control systems (e.g., his brain) find more efficient ways of speaking with the correct amplitude. Any motor overflow, including over-activity of the system being practiced or another system, is therefore often only a temporary side effect of this therapy. The presence of motor overflow may even indicate to a therapist that the therapy is stimulating the correct motor system (e.g. a system controlling speech or movement) even though it is also stimulating an incorrect motor system as well.

Therapy techniques that use loud voices and big movement, for example, are effective in treating many types of symptoms and diseases, including those where the patient suffers from decreased amplitude or incoordination of speech or movements. Working with larger amplitude (e.g., louder, bigger) speech or movement can allow the therapist to more easily train and guide a patient in the correct performance of the task. The larger amplitude of the patient's performance can also allow a therapist to distinguish between parts of the performance that need to be "shaped" or corrected, and parts that may correct themselves as the therapy proceeds (e.g., motor overflow).

Larger amplitude therapy techniques can be used in many applications. These therapy techniques have the benefit and advantage of being almost universally applicable to a patient's life. Thus, the therapy techniques described herein can be used in many different settings and applications, including follow-up or maintenance therapy sessions performed over a phone call. Patients can benefit from any level of therapy program using the methods and apparatus herein. For example, a patient may have already learned several fundamental skills and adapted them for use in many situations in his life (e.g., complex tasks). A therapy session may provide this patient with reminders and examples of how to use these fundamental skills. The therapy session may also help the patient recalibrate his perception. Another patient may only be exposed to a brief encounter with a therapist in a virtual therapy session, yet may experience increased mobility and speed through applying the fundamental skill of moving with deliberately larger movements than her perception tells her is necessary. The patient could receive positive benefit through this behavioral treatment method and apparatus simply by being exposed to the therapy briefly, learning a fundamental skill, and repeatedly applying it in an area of her life.

The therapy techniques also provide important cross benefits, for example, improvement in strength training and muscle coordination which can help speech quality. These cross linkages between treatment goals of the behavioral treatment method and apparatus are important element of a cross functional therapy program. Even when the therapy program is not directed at cross functional goals, however, there may be some side benefits obtained. For example, speech therapy in cerebral palsy patients may reduce spastic motor movements. However, when the behavioral treatment method and apparatus focus on training or providing therapy for more than one functional type of performance (e.g., speech and movement together), both functional types may show improvement beyond what could be attained by focusing on one or the other.

Using complex tasks is another advantage of these therapy techniques. The therapist uses a patient's understanding of the complex task to help the patient perform more tasks and more complex tasks earlier in the therapy program. Unlike traditional therapies that isolate skills by breaking up complex tasks into simple tasks, using complex tasks allows the patient to practice many tasks at the same time. For example, a patient suffering from a speech related disorder may suffer simultaneously from decreased vocal quality, vocal loudness, mumbled speech articulation, and facial expressions. Practicing each one of these individually may be possible, as may be putting together these four types of skills afterward (traditional speech therapy approaches). However, through training the fundamental skill of speaking louder and ONLY speaking LOUDER, the patient may from the beginning of the therapy program practice all four types of skills at the same time. Through the speech therapist observing the patient and understanding what parts of the patient's performance need to be corrected, and which may be ignored as motor overflow, the therapist may allow the patient to continue practicing a complex skill, with a single patient focus on loudness, while adjusting and guiding the patient's performance. Therefore, the patient may continue to practice a complex skill in its entirety before all the parts are refined. Neurologically this provides benefits for the patient's rehabilitation in that neural circuits in the brain may be trained simultaneously with transference of positive benefits across systems. The patient also does not have to think about how to break apart the skills of voice volume, voice quality, mumbled articulation, and facial expression nor does she have to think about how to put those speech-related skills together again. The therapeutic method and apparatus can also train multiple levels and/or types of skills through the training of complex skills and, therefore, the benefits of training complex skills are not limited to the task of speaking clearly while using correct facial expression or even to the task of walking through an area full of obstacles (e.g., chairs, boxes) while having a casual conversation with a therapist.

The effectiveness of these therapy techniques can also reduce their cost. For example a four-week intervention-type therapy program combined with weekly continuation phone calls can provide quick, relatively inexpensive results for patient. Using some of the virtual therapy techniques described above can provide further cost-saving benefits. Furthermore, the use of complex skills that are relevant and applicable to the patient's life allows the patient to use those complex skills directly, thereby reducing any costs associated with continuing the therapy in order to help the patient integrate the therapy into his life.

It is believed that no other treatment program focuses solely on the amplitude of the movements. This may be beneficial because if the patient can make large-amplitude movements they will automatically become faster and will be practicing dynamic balance (within the context of functional movements) and will be practicing a greater variety of coordinative movements, without even focusing on those issues.

It is believed that speech and physical therapy have not previously been performed on a patient simultaneously by one therapist. Further, traditional treatment for Parkinson's disease taught that the patient should never be given two tasks to do at once. Further, the use of explicit calibration, embedded internal calibration or internal cues (i.e., think big/think loud) for a Parkinson's patient is believed to be novel.

The standardized protocol can be used on different patients across a wide range of variation in severity of their speech or movement disorder. Further, the process is more intense (higher effort/more repetitions/progressive) than other treatment programs, resulting in the amount of practice shown to produce learning (i.e., plasticity) in the brain. Patients develop confidence, become overly familiar with, and experience success in these fundamental tasks, termed "overlearning." The process also holds patients accountable through homework and carryover assignments.

A group of related but distinct therapy techniques (Lee Silverman Voice Treatment or LSVT) have been developed in the past by some of the inventors named on this application. Prior to the development of the behavioral treatment method and apparatus described herein, the best available treatment method was LSVT. LSVT was developed for the treatment of Parkinson's disease and relates solely to speech and speech related treatments. LSVT involves intervention treatment only, and was designed for the clinical application of perturbing a patient's system and clinically evaluating the impact on the patient's system afterward. LSVT also uses explicit calibration instructions, such as, the therapist asking "how loud did that feel?" Therefore, a patient may only be required to be "loud" in LSVT when he knew he was performing a task.

Another group of related but distinct therapy techniques are co-therapy techniques. Co-therapy programs are designed for treating patients with deficiencies in several areas, such as speech and movement. Co-therapy is often performed in the presence of multiple therapists, one devoted to each discipline being trained. A co-therapy session may include some speech tasks and some movement tasks observed by the relevant therapist trained in guiding those tasks. The speech tasks in co-therapy programs are separated from the movement tasks and vise versa. The two types of tasks are kept separate (e.g., are not combined) for reasons such as to avoid confusing the patient, and/or to avoid going outside of the range of expertise of the therapist presently observing the patient. Much of the literature in the field of treating neurological disorders prior to the development of this behavioral treatment method and apparatus cautioned against the use of complex tasks or "dual tasks" for many of the same reasons.

The foregoing description of the present invention has been presented for purposes of illustration and description. Furthermore, the description is not intended to limit the invention to the form disclosed herein. While a number of exemplary aspects and embodiments have been discussed above, those of skill in the art will recognize certain variations, modifications, permutations, additions, and sub-combinations thereof. It is therefore intended that the following appended claims and claims hereafter introduced are interpreted to include all such variations, modifications, permutations, additions, and sub-combinations as are within their true spirit and scope.

What is claimed:

1. A method of determining amplitudes for treating symptoms of a neurological disorder, neurological condition, or effects of natural aging process, comprising steps of:
   instructing for a patient to perform a first combined vocal and movement task simultaneously while focusing on amplitudes of the first combined vocal and movement task, wherein the amplitudes include a sound pressure level and a size of body movements the patient generates;
   the patient performing the combined vocal and movement task as instructed in the instructing step; and
   using a computer, microphone, and display screen to perform sensory calibration, wherein the sensory calibration includes:
   determining the amplitude of the first vocal task by taking measurements of a sound pressure level with the computer and microphone;
   displaying the measured sound pressure level on the display screen;
   determining the amplitude of the first movement task by observing the size of the body movements the patient generates;
   asking the patient to describe a perceived effort of amplitudes related to the determined amplitudes of the first combined vocal and movement task as performed;
   determining a fit between the perceived effort of amplitudes of the first combined vocal and movement task and the determined amplitudes of the first combined vocal and movement task; and
   communicating with the patient a sensory calibrating instruction based on the fit;
   wherein symptoms of a neurological disorder, neurological condition, or effects of natural aging are treated.

2. The method as defined in claim 1, wherein the asking step includes a request to perform a second combined vocal and movement task.

3. The method as defined in claim 2, further including providing an instruction wherein the patient is reminded to focus on amplitude and the perceived effort of amplitude if the patient does not perform the second combined vocal and movement task at a sufficient amplitude.

4. The method as defined in claim 1, further including giving a pre-task sensory calibrating instruction before the instructing.

5. The method as defined in claim 1, wherein the step of performing sensory calibration includes directing the patient to perform the first combined vocal and movement task again while attempting to attain a different perceived amplitude.

6. The method as defined in claim 1, wherein the first combined vocal and movement task is a compound vocal and movement task.

7. The method as defined in claim 1, wherein the first combined vocal and movement task is a combined vocal and movement task suggested by the patient.

8. The method as defined in claim 1, wherein all of the therapy is performed by a single therapist.

9. The method of claim 4, further comprising steps of:
   having the patient perform the same core combined vocal and movement tasks at each of multiple therapy sessions in at least a first period, a second period, and a third period of a treatment plan for the patient;
   further having the patient perform different hierarchical combined vocal and movement tasks at the multiple therapy sessions in at least the first period, the second period, and the third period of the treatment plan for the patient.

10. The method of claim 1, further comprising a step of: displaying the first movement task on the display screen.

11. A method of determining amplitudes for treating symptoms of a neurological disorder, neurological condition, or effects of natural aging process, comprising steps of:
   instructing for a patient to perform a first combined vocal and movement task simultaneously while focusing on amplitudes of the first combined vocal and movement task, wherein the amplitudes include a sound pressure level and a size of body movements the patient generates;
   the patient performing the combined vocal and movement task as instructed in the instructing step; and using a sound pressure level meter and display screen to perform sensory calibration, wherein the sensory calibration includes:
determining the amplitude of the first vocal task by taking measurements of a sound pressure level with the sound pressure level meter;
displaying the measured sound pressure level on the display screen;
determining the amplitude of the first movement task by observing the size of the body movements the patient generates;
asking the patient to describe a perceived effort of amplitudes related to the determined amplitudes of the first combined vocal and movement task as performed;
determining a fit between the perceived effort of amplitudes of the first combined vocal and movement task and the determined amplitudes of the first combined vocal and movement task; and
communicating with the patient a sensory calibrating instruction based on the fit;
wherein symptoms of a neurological disorder, neurological condition, or effects of natural aging are treated.

12. The method as defined in claim 11, wherein the asking step includes a request to perform a second combined vocal and movement task.

13. The method as defined in claim 11, further including providing an instruction wherein the patient is reminded to focus on amplitude and the perceived effort of amplitude if the patient does not perform the second combined vocal and movement task at a sufficient amplitude.

14. The method as defined in claim 11, further including giving a pre-task sensory calibrating instruction before the instructing.

15. The method as defined in claim 11, wherein the step of performing sensory calibration includes directing the patient to perform the combined vocal and movement task again while attempting to attain a different perceived amplitude.

16. The method as defined in claim 11, wherein the first combined vocal and movement task is a compound vocal and movement task.

17. The method as defined in claim 11, wherein the first combined vocal and movement task is a combined vocal and movement task suggested by the patient.

18. The method as defined in claim 11, wherein all of the therapy is performed by a single therapist.

19. The method of claim 11, further comprising steps of:
having the patient perform the same core combined vocal and movement tasks at each of multiple therapy sessions in at least a first period, a second period, and a third period of a treatment plan for the patient; and
further having the patient perform different hierarchical combined vocal and movement tasks at the multiple therapy sessions in at least the first period, the second period, and the third period of the treatment plan for the patient.

20. The method of claim 11, further comprising a step of:
displaying the first movement task on the display screen.

* * * * *